United States Patent
Simpson et al.

(10) Patent No.: US 9,572,492 B2
(45) Date of Patent: Feb. 21, 2017

(54) OCCLUSION-CROSSING DEVICES, IMAGING, AND ATHERECTOMY DEVICES

(71) Applicant: Avinger, Inc., Redwood City, CA (US)

(72) Inventors: John B. Simpson, Woodside, CA (US); Himanshu N. Patel, San Jose, CA (US); Michael Zung, San Carlos, CA (US); Charles W. McNall, Salt Lake City, UT (US); Priyanshu Gupta, Palo Alto, CA (US); Maegan K. Spencer, Emerald Hills, CA (US); Christopher B. White, San Jose, CA (US); Dennis W. Jackson, San Francisco, CA (US); John F. Black, San Mateo, CA (US)

(73) Assignee: Avinger, Inc., Redwood City, CA (US)

( * ) Notice: Subject to any disclaimer, the term of this patent is extended or adjusted under 35 U.S.C. 154(b) by 381 days.

(21) Appl. No.: 14/171,583

(22) Filed: Feb. 3, 2014

(65) Prior Publication Data
US 2014/0213893 A1    Jul. 31, 2014

Related U.S. Application Data

(63) Continuation of application No. 13/433,049, filed on Mar. 28, 2012, now Pat. No. 8,644,913.
(Continued)

(51) Int. Cl.
*A61B 5/00* (2006.01)
*A61B 17/3207* (2006.01)
(Continued)

(52) U.S. Cl.
CPC .......... *A61B 5/0035* (2013.01); *A61B 5/0062* (2013.01); *A61B 5/0066* (2013.01); *A61B 5/0084* (2013.01);
(Continued)

(58) Field of Classification Search
None
See application file for complete search history.

(56) References Cited

U.S. PATENT DOCUMENTS

| | | | |
|---|---|---|---|
| 4,178,935 A | 12/1979 | Gekhaman et al. | |
| 4,527,553 A | 7/1985 | Upsher | |

(Continued)

FOREIGN PATENT DOCUMENTS

| | | |
|---|---|---|
| CN | 1875242 A | 12/2006 |
| CN | 1947652 A | 4/2007 |

(Continued)

OTHER PUBLICATIONS

Aziz et al.; Chronic total occlusions—a stiff challenge requiring a major breakthrough: is there light at the end of the tunnel?; Heart; vol. 91; suppl. III; pp. 42-48; Jun. 2005.
(Continued)

*Primary Examiner* — Long V Le
*Assistant Examiner* — Bradley Impink
(74) *Attorney, Agent, or Firm* — Shay Glenn LLP

(57) ABSTRACT

A catheter device for crossing occlusions includes an elongate body, a central lumen extending within the elongate body from the proximal end to the distal end, a rotatable tip at the distal end of the elongate body, and an OCT imaging sensor. The rotatable tip is configured to rotate relative to the elongate body. The OCT imaging sensor includes an optical fiber coupled with the rotatable tip and configured to rotate therewith. A distal end of the elongate body includes one or more markers configured to occlude the OCT imaging sensor as it rotates. A fixed jog in the elongate body proximal to the distal end of the catheter positions the distal end of the catheter at an angle relative to the region of the catheter proximal to the fixed jog and is aligned with the one or more markers on the elongate body.

10 Claims, 30 Drawing Sheets

Related U.S. Application Data

(60) Provisional application No. 61/468,396, filed on Jan. 28, 2011, provisional application No. 61/548,179, filed on Oct. 17, 2011.

(51) Int. Cl.

| | | |
|---|---|---|
| *A61B 5/02* | (2006.01) | |
| *A61B 6/12* | (2006.01) | |
| *A61B 17/32* | (2006.01) | |
| *A61B 17/22* | (2006.01) | |
| *A61B 17/00* | (2006.01) | |
| *A61B 6/00* | (2006.01) | |
| *A61B 8/08* | (2006.01) | |

(52) U.S. Cl.
CPC ......... *A61B 5/02007* (2013.01); *A61B 5/4836* (2013.01); *A61B 5/6852* (2013.01); *A61B 6/12* (2013.01); *A61B 6/485* (2013.01); *A61B 17/32002* (2013.01); *A61B 17/320758* (2013.01); *A61B 90/37* (2016.02); *A61B 90/39* (2016.02); *A61B 6/487* (2013.01); *A61B 8/0841* (2013.01); *A61B 2017/003* (2013.01); *A61B 2017/00057* (2013.01); *A61B 2017/00778* (2013.01); *A61B 2017/22068* (2013.01); *A61B 2090/306* (2016.02); *A61B 2090/3614* (2016.02); *A61B 2090/3735* (2016.02); *A61B 2090/3966* (2016.02); *A61B 2217/007* (2013.01); *A61B 2562/0233* (2013.01); *F04C 2270/0421* (2013.01)

(56) References Cited

U.S. PATENT DOCUMENTS

| | | | |
|---|---|---|---|
| 4,552,554 A | 11/1985 | Gould et al. | |
| 4,621,353 A | 11/1986 | Hazel et al. | |
| 4,639,091 A | 1/1987 | Huignard et al. | |
| 4,654,024 A | 3/1987 | Crittenden et al. | |
| 4,686,982 A | 8/1987 | Nash | |
| 4,771,774 A | 9/1988 | Simpson et al. | |
| 4,841,977 A | 6/1989 | Griffith et al. | |
| 4,926,858 A | 5/1990 | Gifford, III et al. | |
| 5,000,185 A | 3/1991 | Yock | |
| 5,041,082 A | 8/1991 | Shiber | |
| 5,047,040 A | 9/1991 | Simpson et al. | |
| 5,085,662 A | 2/1992 | Willard | |
| 5,099,850 A | 3/1992 | Matsui et al. | |
| 5,178,153 A | 1/1993 | Einzig | |
| 5,182,291 A | 1/1993 | Gubin et al. | |
| 5,190,050 A | 3/1993 | Nitzsche | |
| 5,192,291 A | 3/1993 | Pannek, Jr. | |
| 5,312,415 A | 5/1994 | Palermo | |
| 5,312,425 A | 5/1994 | Evans et al. | |
| 5,321,501 A | 6/1994 | Swanson et al. | |
| 5,333,142 A | 7/1994 | Scheps | |
| 5,358,472 A | 10/1994 | Vance et al. | |
| 5,366,464 A | 11/1994 | Belknap | |
| 5,383,460 A | 1/1995 | Jang et al. | |
| 5,383,467 A | 1/1995 | Auer et al. | |
| 5,429,136 A | 7/1995 | Milo et al. | |
| 5,431,673 A | 7/1995 | Summers et al. | |
| 5,459,570 A | 10/1995 | Swanson et al. | |
| 5,465,147 A | 11/1995 | Swanson | |
| 5,507,795 A | 4/1996 | Chiang et al. | |
| 5,556,405 A | 9/1996 | Lary | |
| 5,632,754 A | 5/1997 | Farley et al. | |
| 5,632,755 A | 5/1997 | Nordgren et al. | |
| 5,674,232 A | 10/1997 | Halliburton | |
| 5,681,336 A | 10/1997 | Clement et al. | |
| 5,690,634 A | 11/1997 | Muller et al. | |
| 5,722,403 A | 3/1998 | McGee et al. | |
| 5,795,295 A | 8/1998 | Hellmuth et al. | |
| 5,807,339 A | 9/1998 | Bostrom et al. | |
| 5,830,145 A | 11/1998 | Tenhoff | |
| 5,836,957 A | 11/1998 | Schulz et al. | |
| 5,843,050 A | 12/1998 | Jones et al. | |
| 5,868,778 A | 2/1999 | Gershony et al. | |
| 5,872,879 A | 2/1999 | Hamm | |
| 5,904,651 A | 5/1999 | Swanson et al. | |
| 5,907,425 A | 5/1999 | Dickensheets et al. | |
| 5,935,075 A | 8/1999 | Casscells et al. | |
| 5,938,602 A | 8/1999 | Lloyd | |
| 5,951,482 A | 9/1999 | Winston et al. | |
| 5,951,581 A | 9/1999 | Saadat et al. | |
| 5,951,583 A | 9/1999 | Jensen et al. | |
| 5,956,355 A | 9/1999 | Swanson et al. | |
| 5,957,952 A | 9/1999 | Gershony et al. | |
| 5,987,995 A | 11/1999 | Sawatari et al. | |
| 5,997,558 A | 12/1999 | Nash | |
| 6,001,112 A | 12/1999 | Taylor | |
| 6,007,530 A | 12/1999 | Dornhofer et al. | |
| 6,010,449 A | 1/2000 | Selmon et al. | |
| 6,013,072 A | 1/2000 | Winston et al. | |
| 6,017,359 A | 1/2000 | Gershony et al. | |
| 6,027,514 A | 2/2000 | Stine et al. | |
| 6,032,673 A | 3/2000 | Savage et al. | |
| 6,048,349 A | 4/2000 | Winston et al. | |
| 6,080,170 A | 6/2000 | Nash et al. | |
| 6,106,515 A | 8/2000 | Winston et al. | |
| 6,110,164 A | 8/2000 | Vidlund | |
| 6,120,515 A | 9/2000 | Rogers et al. | |
| 6,120,516 A | 9/2000 | Selmon et al. | |
| 6,134,002 A | 10/2000 | Stimson et al. | |
| 6,134,003 A | 10/2000 | Tearney et al. | |
| 6,152,938 A | 11/2000 | Curry | |
| 6,152,951 A | 11/2000 | Hashimoto et al. | |
| 6,160,826 A | 12/2000 | Swanson et al. | |
| 6,175,669 B1 | 1/2001 | Colston et al. | |
| 6,176,871 B1 | 1/2001 | Pathak et al. | |
| 6,183,432 B1 | 2/2001 | Milo | |
| 6,193,676 B1 | 2/2001 | Winston et al. | |
| 6,206,898 B1 | 3/2001 | Honeycutt et al. | |
| 6,228,076 B1 | 5/2001 | Winston et al. | |
| 6,241,744 B1 | 6/2001 | Imran et al. | |
| 6,283,957 B1 | 9/2001 | Hashimoto et al. | |
| 6,290,668 B1 | 9/2001 | Gregory et al. | |
| 6,294,775 B1 | 9/2001 | Seibel et al. | |
| 6,299,622 B1 | 10/2001 | Snow et al. | |
| 6,307,985 B1 | 10/2001 | Murakami et al. | |
| 6,402,719 B1 | 6/2002 | Ponzi et al. | |
| 6,416,527 B1 | 7/2002 | Berg et al. | |
| 6,445,939 B1 | 9/2002 | Swanson et al. | |
| 6,445,944 B1 | 9/2002 | Ostrovsky | |
| 6,447,525 B2 | 9/2002 | Follmer et al. | |
| 6,451,036 B1 | 9/2002 | Heitzmann et al. | |
| 6,454,779 B1 | 9/2002 | Taylor | |
| 6,482,217 B1 | 11/2002 | Pintor et al. | |
| 6,485,413 B1 | 11/2002 | Boppart et al. | |
| 6,497,649 B2 | 12/2002 | Parker et al. | |
| 6,501,551 B1 | 12/2002 | Tearney et al. | |
| 6,503,261 B1 | 1/2003 | Bruneau et al. | |
| 6,511,458 B2 | 1/2003 | Milo et al. | |
| 6,517,528 B1 | 2/2003 | Patages et al. | |
| 6,542,665 B2 | 4/2003 | Reed et al. | |
| 6,546,272 B1 | 4/2003 | MacKinnon et al. | |
| 6,551,302 B1 | 4/2003 | Rosinko et al. | |
| 6,563,105 B2 | 5/2003 | Seibel et al. | |
| 6,564,087 B1 * | 5/2003 | Pitris ................. A61B 1/00183 600/478 |
| 6,565,588 B1 | 5/2003 | Clement et al. | |
| 6,572,563 B2 | 6/2003 | Ouchi et al. | |
| 6,572,643 B1 | 6/2003 | Gharibadeh | |
| 6,575,995 B1 | 6/2003 | Huter et al. | |
| 6,579,298 B1 | 6/2003 | Bruneau et al. | |
| 6,615,071 B1 | 9/2003 | Casscells, III et al. | |
| 6,638,233 B2 | 10/2003 | Corvi et al. | |
| 6,645,217 B1 | 11/2003 | MacKinnon et al. | |
| 6,666,874 B2 | 12/2003 | Heitzmann et al. | |
| 6,687,010 B1 | 2/2004 | Horii | |
| 6,728,571 B1 | 4/2004 | Barbato | |
| D489,973 S | 5/2004 | Root et al. | |
| 6,730,063 B2 | 5/2004 | Delaney et al. | |

(56) References Cited

U.S. PATENT DOCUMENTS

| | | | |
|---|---|---|---|
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,644,913 B2 | 2/2014 | Simpson et al. |
| 8,696,695 B2 | 4/2014 | Patel et al. |
| 2001/0020126 A1 | 9/2001 | Swanson et al. |
| 2002/0019644 A1 | 2/2002 | Hastings et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120295 A1* | 6/2003 | Simpson ........ A61B 17/320758 606/159 |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0082850 A1 | 4/2004 | Bonner et al. |
| 2004/0092915 A1 | 5/2004 | Levatter |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0015126 A1* | 1/2006 | Sher ............... A61B 17/320758 606/159 |
| 2006/0032508 A1 | 2/2006 | Simpson |
| 2006/0046235 A1 | 3/2006 | Alexander |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |

(56) References Cited

U.S. PATENT DOCUMENTS

| | | |
|---|---|---|
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1* | 1/2008 | To ................ A61B 17/32075 606/159 |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0040238 A1 | 2/2011 | Wulfman et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0301625 A1 | 12/2011 | Mauch et al. |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0289392 A1 | 10/2013 | Patel et al. |
| 2013/0296695 A1 | 11/2013 | Spencer et al. |
| 2014/0005534 A1 | 1/2014 | He et al. |
| 2016/0192962 A1 | 7/2016 | Simpson et al. |
| 2016/0199092 A1 | 7/2016 | Patel et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-225349 A | 9/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-78150 A | 4/2009 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO 01/76680 A1 | 10/2001 |
| WO | WO 2006/133030 A2 | 12/2006 |
| WO | WO 2008/029506 A | 3/2008 |
| WO | WO 2008/042987 A2 | 4/2008 |
| WO | WO 2008/065600 A2 | 6/2008 |
| WO | WO 2008/086613 A1 | 7/2008 |
| WO | WO 2008/087613 A2 | 7/2008 |
| WO | WO 2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2010/039464 A1 | 4/2010 |
| WO | WO2010/056771 A1 | 5/2010 |
| WO | WO 2012/061935 A1 | 5/2012 |

(56) References Cited

OTHER PUBLICATIONS

Emkey et al.; Analysis and evaluation of graded-index fiber-lenses; Journal of Lightwave Technology; vol. LT-5; No. 9; pp. 1156-1164; Sep. 1987.

Linares et al.; Arbitrary single-mode coupling by tapered and nontapered grin fiber lenses; Applied Optics; vol. 29; No. 28; pp. 4003-4007; Oct. 1, 1990.

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Wang et al.; Common-path endoscopic Fourier domain OCT with a reference Michelson interferometer; Proceedings of the SPIE; vol. 7566; pp. 75660L-75660L-7; Jan. 2010.

Gonzalo et al.; Optical coherence tomography patterns of stent restenosis; Am. Heart J.; 158(2); pp. 284-293; Aug. 2009.

Tanaka et al.; Challenges on the frontier of intracoronary imaging: atherosclerotic plaque macrophage measurement by optical coherence tomography; Journal of Biomedical Optics; 15(1); pp. 011104-1-011104-8; Jan.-Feb. 2010.

Kankaria; U.S. Appl. No. 14/400,140 entitled "Optical coherence tomography with index fiber for biological imaging," filed Nov. 10, 2014.

Gupta et al.; U.S. Appl. No. 14/401,175 entitled "Atherectomy catheters with imaging," filed Nov. 14, 2014.

Tachibana et al.; U.S. Appl. No. 14/400,151 entitled "Atherectomy catheter drive assemblies," filed Nov. 10, 2014.

Simpson et al.; U.S. Appl. No. 14/424,266 entitled "Re-entry stylet for catheter," filed Feb. 26, 2015.

Simpson et al.; U.S. Appl. No. 14/424,277 entitled "Balloon atherectomy catheters with imaging," filed Feb. 26, 2015.

Newhauser et al.; U.S. Appl. No. 14/433,786 entitled "Occusion-crossing devices," filed Apr. 6, 2015.

Gupta et al.; U.S. Appl. No. 14/776,749 entitled "Tissue collection device for catheter," filed Sep. 15, 2015.

Smith et al.; U.S. Appl. No. 14/776,750 entitled "Chronic total occlusion crossing devices with imaging," filed Sep. 15, 2015.

Smith et al.; U.S. Appl. No. 14/776,748 entitled "Optical pressure sensor assembly," filed Sep. 15, 2015.

Simpson et al.; U.S. Appl. No. 14/899,877 entitled "Occusion sheath for imaging catheter," filed Dec. 18, 2015.

Simpson et al.; U.S. Appl. No. 14/899,893 entitled "Identification of elastic lamina to guide interventional therapy," filed Dec. 18, 2015.

Patel et al.; U.S. Appl. No. 15/162,330 entitled "Atherectomy catheters with longitudinally displaceable drive shafts," filed May 23, 2016.

Spencer et al.; U.S. Appl. No. 15/162,353 entitled "Occlusion-crossing devices, atherectomy devices, and imaging," filed May 23, 2016.

Tachibana et al.; U.S. Appl. No. 15/162,391 entitled "Atherectomy catheter drive assemblies," filed May 23, 2016.

\* cited by examiner

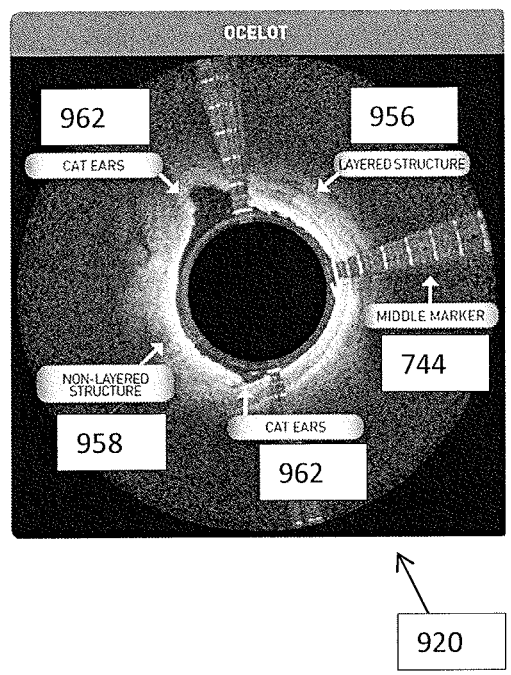
FIG. 9A
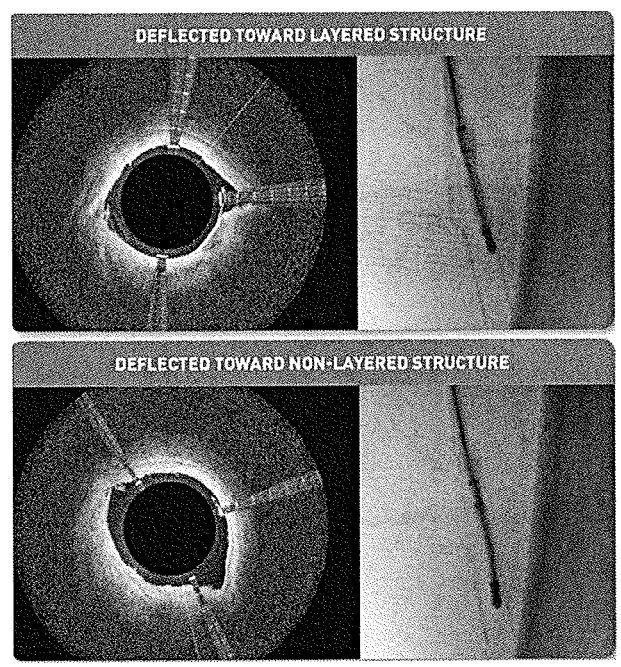
FIG. 9B
FIG. 9C

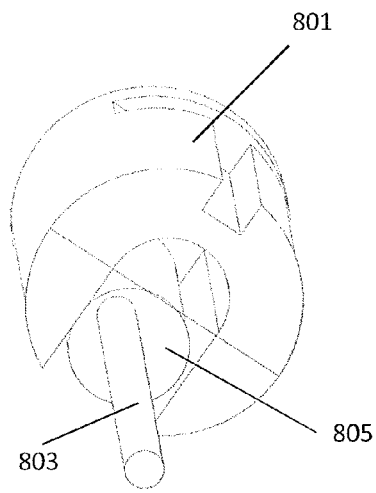
FIG. 13A
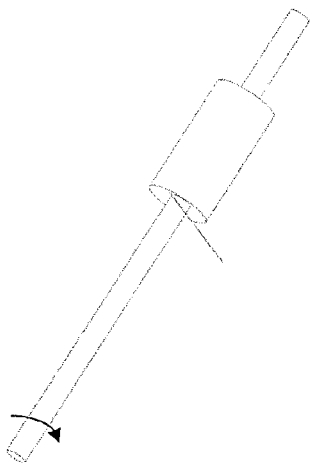 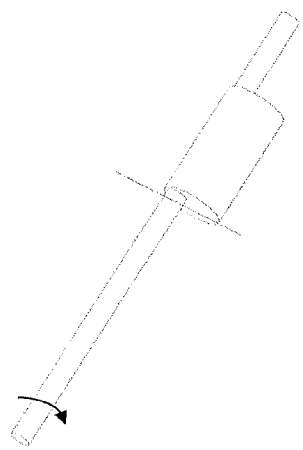 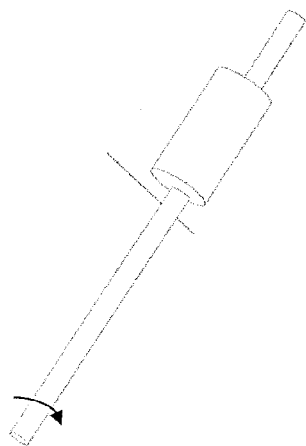
FIG. 13B    FIG. 13C    FIG. 13D

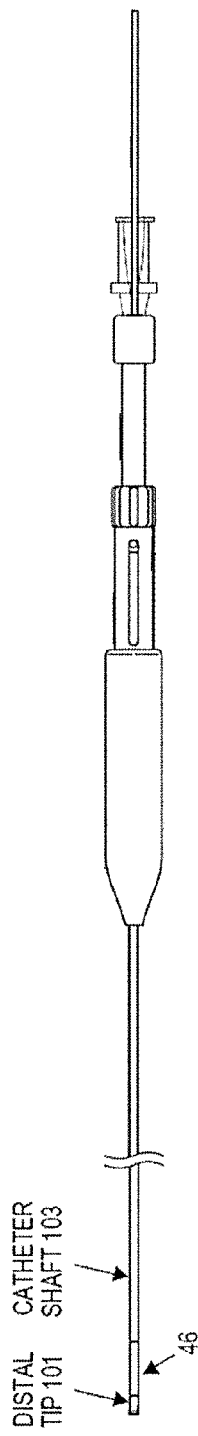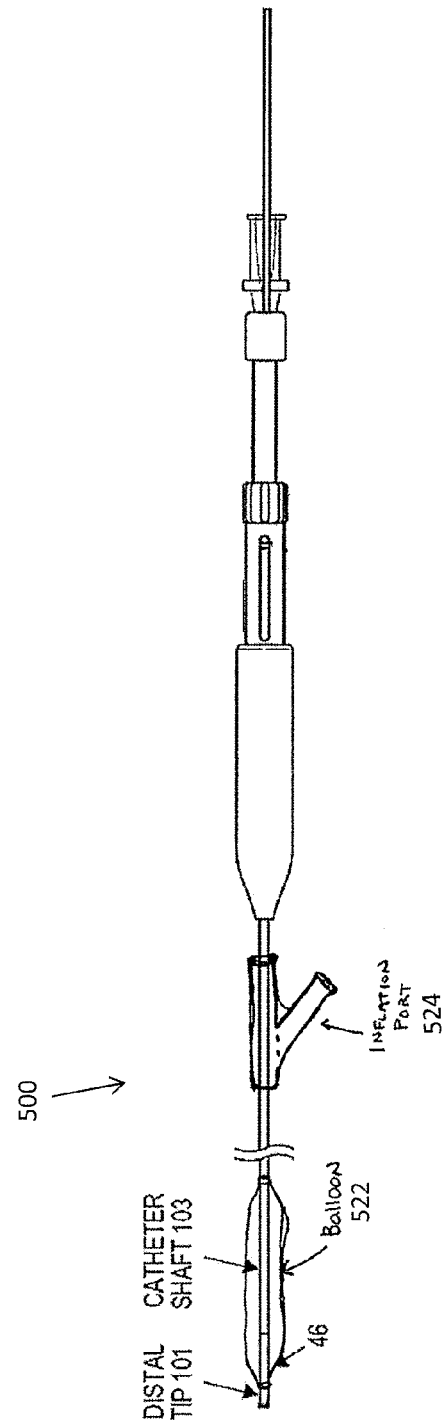
FIG. 15A
FIG. 15B

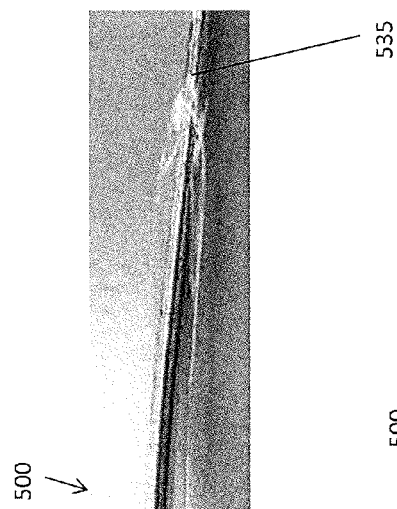
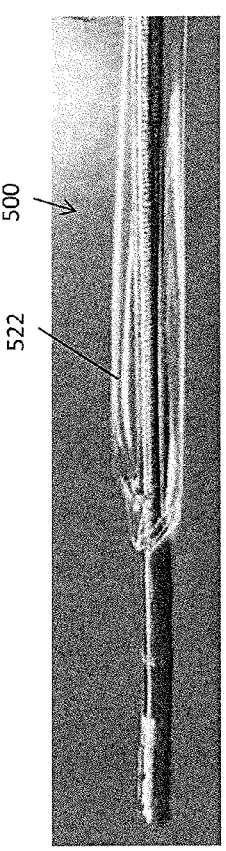
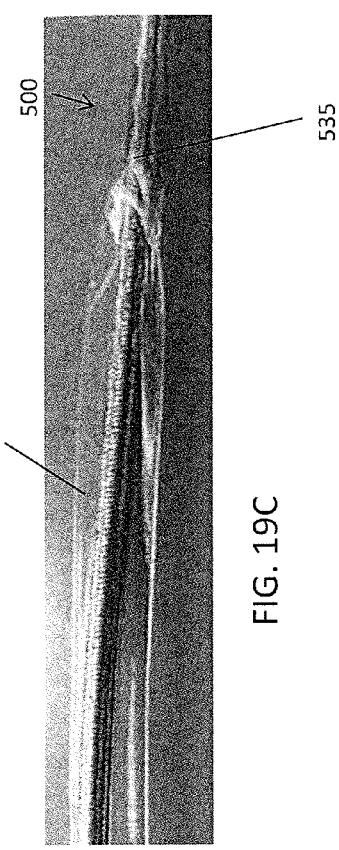
FIG. 19A
FIG. 19B
FIG. 19C

OCCLUSION-CROSSING DEVICES, IMAGING, AND ATHERECTOMY DEVICES

CROSS REFERENCE TO RELATED APPLICATIONS

This application is a continuation of U.S. patent application Ser. No. 13/433,049, filed Mar. 28, 2012, titled "OCCLUSION-CROSSING DEVICES, IMAGING, AND ATHERECTOMY DEVICES," now U.S. Pat. No. 8,644,913 which claims priority to U.S. Patent Provisional Application No. 61/468,396, filed Mar. 28, 2011 and titled "OCCLUSION-CROSSING DEVICES, IMAGING, AND ATHERECTOMY DEVICES" and U.S. Patent Provisional Application No. 61/548,179, filed Oct. 17, 2011 and titled "OCCLUSION-CROSSING DEVICES, IMAGING, AND ATHERECTOMY DEVICES," herein incorporated by reference.

This patent application may be related to one or more of the following pending patent applications: U.S. patent application Ser. No. 12/689,748, filed Jan. 19, 2010 and titled "GUIDEWIRE SUPPORT CATHETER", Publication No. US-2010-0274270-A1; U.S. patent application Ser. No. 12/108,433, filed Apr. 23, 2008 and titled "CATHETER SYSTEM AND METHOD FOR BORING THROUGH BLOCKED VASCULAR PASSAGES", now U.S. Pat. No. 8,062,316; U.S. patent application Ser. No. 12/272,697, filed Nov. 17, 2008 and titled "DUAL-TIP CATHETER SYSTEM FOR BORING THROUGH BLOCKED VASCULAR PASSAGES", Publication No. US-2010-0125253-A1, now abandoned; U.S. patent application Ser. No. 12/829,277, filed Jul. 1, 2010 and titled "ATHERECTOMY CATHETER WITH LATERALLY-DISPLACEABLE TIP", Publication No. US-2011-0004107-A1; U.S. patent application Ser. No. 12/829,267, filed Jul. 1, 2010 and titled "CATHETER-BASED OFF-AXIS OPTICAL COHERENCE TOMOGRAPHY IMAGING SYSTEM", Publication No. US-2010-0021926-A1; U.S. patent application Ser. No. 12/790,703, filed May 28, 2010 and titled "OPTICAL COHERENCE TOMOGRAPHY FOR BIOLOGICAL IMAGING", Publication No. US-2010-0305452-A1; and U.S. patent application Ser. No. 12/963,536, filed Dec. 8, 2010 and titled "DEVICES AND METHODS FOR PREDICTING AND PREVENTING RESTENOSIS", Publication No. US-2011-0263836-A1. Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are catheters and specifically, catheters that may include a rotating distal tip having both a directional cutting element and an OCT imaging sensor, an inner lumen for a guidewire extending the length of the catheter, and an optical fiber that is configured to wind and unwind within the catheter as the OCT imaging sensor at the distal end rotates. The catheters described herein may be configured as one or more of: guidewire support and/or placement catheters, imaging catheters, atherectomy catheters, chronic total occlusion crossing catheters, and hybrid support/placement catheters with imaging and/or atherectomy features. Methods of using the catheters described herein are also provided.

BACKGROUND

Peripheral artery disease (PAD) affects millions of people in the United States alone. PAD is a silent, dangerous disease that can have catastrophic consequences when left untreated. PAD is the leading cause of amputation in patients over 50 and is responsible for approximately 160,000 amputations in the United States each year.

Peripheral artery disease (PAD) is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease.

Interventional treatments for PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

Such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

If imaging is used to assist in placement of guidewires for treating PAD (including treatment of chronic total occlusion), fluoroscopy is typically used to visualize the location of the lumen of the vessel with respond to the guidewire. However, it would be particularly beneficial to visualize within the lumen of a vessel as the guidewire is placed, both to identify regions for effective therapy as well as to prevent damage to surrounding tissue.

A significant body of scientific and clinical evidence supports atherectomy as a viable primary or adjunctive therapy prior to stenting for the treatment of occlusive coronary artery disease. Atherectomy offers a simple mechanical advantage over alternative therapies. Removing the majority of plaque mass (e.g., debulking) may create a larger initial lumen and dramatically increases the compliance of the arterial wall. As a result, stent deployment is greatly enhanced.

Additionally, there are advantages related to the arterial healing response when selecting atherectomy as a treatment option. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By removing the disease with minimal force applied to the vessel and reducing the plaque burden prior to stent placement, large gains in lumen size can be created with decreased vessel wall injury and limited elastic recoil, all of which have shown to translate into better acute results and lower restenosis rates.

Traditional atherectomy devices have been plagued by a number of problems, which have severely limited market adoption. These challenges include the need for large access devices, rigid distal assemblies that make control and introduction challenging, fixed cut length, unpredictable depth of cut, insufficient tissue collection and removal, and complex operation. The systems and devices described herein may overcome these hurdles and offer physicians a safe, reliable, and simple cutting system that offers the precision required in eccentric lesions, various disease states, and tortuous anatomy.

Despite the potential to improve restenosis rates associated with angioplasty and stenting in the coronary and peripheral vasculature, atherectomy is not commonly performed. The primary reason for this limited use is the cost, complexity, and limited applicability of currently available devices. Many designs are unable to treat the wide range of disease states present in long complex lesions; luminal gain is often limited by the requirement of the physician to introduce multiple devices with increased crossing profiles; tissue collection is either unpredictable or considered unnecessary based on assumptions regarding small particle size and volumes; and optimal debulking is either not possible due to lack of intravascular visualization or requires very long procedure times. Based on these limitations, current devices are likely to perform poorly in the coronary vasculature where safety and efficacy in de novo lesions, ostials, and bifurcations continue to pose great challenges.

Previously, atherectomy devices focused on macerating or emulsifying the atherosclerotic plaque such that it may be considered clinically insignificant and remain in the blood stream or aspirated proximally through small spaces in the catheter main body. The reliability of these devices to produce clinically insignificant embolization has been questioned when not aspirated through the catheter to an external reservoir. Aspiration requires a vacuum be applied to a lumen or annular space within the catheter to remove emulsified tissue. In early clinical evaluations of aspiration, the presence of negative pressure at the distal working assembly cause the artery to collapse around the cutting element causing more aggressive treatment, dissections and/or perforations. In addition, the option for post procedural analysis of any removed disease is extremely limited or impossible. Atheromed, Pathway Medical and Cardio Vascular Systems, Inc. are examples of companies working on such product designs.

Other atherectomy devices include the directional atherectomy devices such as those developed by Devices for Vascular Intervention and Fox Hollow. These catheters use cupped cutters that cut and direct the tissue distal into a storage reservoir in the distal tip of the device. This approach preserves the "as cut" nature of the plaque but requires large distal collection elements. These large distal tip assemblies can limit the capabilities of the system to access small lesions and create additional trauma to the vessel.

Currently available atherectomy devices also do not include, and are poorly adapted for use with, real time image guidance. Physician practice is often to treat target lesion as if they contain concentric disease even though intravascular diagnostic devices have consistently shown significantly eccentric lesions. This circumferential treatment approach virtually ensures that native arterial wall and potentially healthy vessel will be cut from the vasculature.

In light of the needs described above, occlusion crossing catheter devices, atherectomy catheter devices, imaging catheters (including imaging guidewire placement devices and imaging atherectomy devices) and systems and methods for using them are described herein in order to address at least some of the concerns described and illustrated above.

SUMMARY OF THE DISCLOSURE

The present invention relates to catheters having a rotating distal tip region that includes an OCT imaging sensor and may include one or more tissue dissecting elements. These catheters may also include a central passage or lumen that opens distally, extending along the length of the catheter body, that may be used to pass a guidewire. In general, the catheters described herein may be configured as: (1) guidewire support/placement catheters; (2) support/placement imaging catheters; (3) occlusion crossing catheters (4) occlusion crossing imaging catheters; (5) atherectomy catheters; and (6) atherectomy imaging catheters. Any of these catheter variations may include one or more of the elements described herein, and any of these catheter variations may be used to treat a disorder, particularly peripheral artery disease. Systems including any of these catheters are also described. For convenience, in the description below, these catheters may be referred to as occlusion crossing catheters. It is to be understood that any of the catheters described herein may be configured as occlusion crossing catheters.

In general, a catheter may include a flexible elongate body, a proximal handle (or handle region), and a distal rotating tip. The distal tip may have a corkscrew-like rotating tip which is configured to rotate to enhance forward motion (e.g., at low rates of rotation) without cutting or drilling through the tissue. Rather than drilling, the tip may be configured to prevent or reduce static friction, avoiding damage to the luminal walls of the vessel and preventing the tip from passing through the adventitia.

The tip may be configured to rotate at very low speeds (e.g., less than about 300 revolutions/min, less than 100 rev/min, less than 50 rev/min, less than 30 rev/min, e.g., between about 1 and about 30 rev/min, etc.) at a constant or variable rate. In many variations, particularly but not necessarily those including an imaging modality (e.g., OCT) with an imaging sensor affixed to the rotating tip, the tip may rotate automatically both clockwise and counterclockwise, alternately. For example, the device or system may be configured to rotate the distal tip first clockwise, then counterclockwise. The clockwise and counterclockwise rotations may be performed continuously for a predetermined number of revolutions or partial revolutions, such as more than one revolution (e.g., approximately 2 revolutions, 2.5 revolutions, 3 revolutions, 5 revolutions, 8 revolutions, 10 revolutions, 12 revolutions, 20 revolutions, 50 revolutions, 100 revolutions, or any number of revolution between 1 and 500, including fractions of revolutions). In some variations, the number of rotations is not predetermined, but may be based on timing or on feedback from the catheter or system. For example, the distal tip (and therefore the OCT imaging sensor) may be rotated in a first direction until a tension or resistance threshold is reached, then rotated in the opposite direction until a tension or resistance threshold is reached in that direction. This process may then be repeated.

Any of the catheters described herein may include one or more tissue dissecting cutting edges on the rotating distal tip. In some variations, the forward edge of the catheter includes one or more helical edges, which may be referred to as wedges. The helical edges may be arranged at the distal end of the device. The edge may have a small diameter, particularly as compared with the ultimate diameter of the device. These edges may be sharp, rough, or otherwise dissecting.

Any of the catheter variations described herein may include a central lumen through which a guidewire may be passed for placement across an occlusion using the device. The central lumen typically extends along the length of the device from the proximal end or a region distal to the proximal end, to the distal end of the catheter. Thus, the catheter may include a distal opening. This central lumen may be referred to as a guidewire lumen. In some variations, the device is configured to pass through a lesion or occlusion (or an occluded region or regions of a vessel) to position the catheter beyond the occlusion before a guidewire is passed through the catheter. Alternatively, the guidewire may be housed or held within the lumen while the device is advanced through the occlusion or occluded region of a vessel, such as an artery, vein, or duct, for example a peripheral artery, vein, or bile duct.

In general, the catheters described herein are configured to apply optical coherence tomography (OCT) to image the tissue. Thus, the catheters described herein can include an imaging sensor, such as an OCT imaging sensor. An OCT imaging sensor may include the distal end of an optical fiber and a mirror for directing light in/out of the optical fiber. The optical fiber may be affixed to the distal tip structure. The imaging sensor may be oriented to image the vessel ahead of the device, perpendicular to the device, and/or behind the device tip. The mirror or reflector may be used to direct the light path entering and exiting the end of the optical fiber to fix the imaging direction for the device. For example, the optical fiber and mirror may be fixed to the rotating distal tip region and may be embedded in a transparent or translucent medium (including transparent cement or other fixative).

An optical fiber of the OCT system can be attached only to the rotating distal tip and at a proximal end but be free to move within the device lumen. As the distal end or tip of the device rotates, the optical fiber may wrap and unwrap around the inner lumen as the distal end/tip is rotated clockwise and counterclockwise. Thus, the length of the optical fiber extending from this affixed region at the rotatable distal tip to the proximal end of the catheter is loose within the catheter body and free to wind/unwind around the catheter body. The inventors have discovered that this loose arrangement of the optical fiber creates advantages compared to systems in which an optical fiber is held along its length or prohibited from off-axis winding, including ease of construction and enhanced catheter flexibility. Thus, any of the catheters described herein may be adapted to allow and control the winding/unwinding of the optical fiber within the catheter, and the optical fiber may be located within the catheter in an off-axis position.

In some variations, the distal end of the device is steerable, pre-bent, or both. For example, the distal end may be biased or curved at an angle off the axis of the shaft. In some variations, a control member (e.g., tendon or other actuator) may be used to control the shape of the distal end. In some variations the catheter includes a prebiased shape or fixed jog so that the distal end of the device (e.g., the rotatable distal tip) forms an angle with the region of the catheter's elongate body immediately proximal to the fixed jog. A fixed jog may help with steering and navigation of the catheter. The jog may be in a plane that is in-line with one or more fiduciary markers that are visible by fluoroscopy or other imaging modality (e.g., ultrasound, etc.).

Any of the catheters configured for imaging described herein may also be configured to enhance the imaging by flushing or otherwise clearing the imaging sensor region so that it may image the vessel wall(s). For example, the catheter may include one or more flush or fluid delivery ports for providing a flushing fluid to clear the visualization pathway for the device. Saline or other flush fluids may be released from the fluid delivery ports to clear the field of view. Flushing may be achieved at a sufficient fluid flow rate to clear help clear the field of view (e.g., by flushing away red blood cells or other material that may inhibit visualization of the vessel walls). The flush port opening(s) at the distal end may be positioned and sized to minimize the amount of fluid (or the fluid flow rate) need to flush the imaging field. Thus, a flush port may be located near the imaging sensor. For example, a flush port may be less than 2 mm from the imaging sensor. Flushing may be controlled manually or automatically.

In some variations, the catheter may have an outer protective housing along the elongate length extending between the distal tip region and the proximal handle or connector region. A space within the outer protective housing and an inner lumen may be referred to as the outer lumen or outer lumen region. An inner lumen, which may be referred to in some variations as a guidewire lumen, may be located within the outer lumen and used to pass the guidewire through the elongate length of the device. The inner lumen may be formed by an internal housing extending along the length of the device. The space between the outer protective housing and the inner lumen may also be referred to as the device lumen. In catheter variations including an optical fiber for imaging, the optical fiber may be housed within the device lumen/outer lumen. Further, in devices including flushing, the flushing fluid can flow through the outer lumen.

Also described herein are catheters including one or more expandable and/or inflatable (e.g., balloon) elements. The inflatable element(s) may be used to help center the distal end of the device within the lumen of the device, helping to prevent the tip of the device from passing through the adventitia. The inflatable member could also be used to limit or prevent the flow of a fluid that would normally block the field of view. In some variations, the expandable/inflatable region may be located near the distal tip of the device, which may include a rotating distal tip/end region.

Also described herein are catheters configured as atherectomy catheters that may also include imaging. For example, describe herein are atherectomy catheters that are side-facing/side-opening and configured to cut occlusive material from a vessel using a circular cutter than can be rotated or oscillated to cut the tissue. Tissue cut in this manner may be stored within the body of the device. The tissue may be masticated or ground up as it is removed.

Specific example of catheters, and particularly occlusion crossing catheters that may be used to place a guidewire across an occlusion, are provided below.

Described herein are catheter devices for crossing chronic total occlusions that include: an elongate body; a guidewire lumen extending within the elongate body from a proximal end of the elongate body to a distal end of the elongate body; a rotatable tip at the distal end of the elongate body and configured to rotate relative to the elongate body; and an OCT imaging sensor comprising an optical fiber coupled with the rotatable tip and configured to rotate therewith, wherein the optical fiber is configured to wrap around the central lumen within the elongate body as the rotatable tip rotates.

These catheter devices may also include a drive mechanism configured to continuously rotate the rotatable tip alternately clockwise then counterclockwise. For example, the drive mechanism may be configured to rotate the rotatable tip at between about 1 and about 100 rotations per minute (rpm), between about 30 and about 60 rpm, or greater than 100 rpm.

A catheter may be configured so that the number of rotations clockwise and counterclockwise is limited. For example, the number of rotations clockwise may be less than 15 rotations before switching to rotate counterclockwise another 15 rotations, then repeating this pattern of rotation. In some variations, the number of clockwise/counterclockwise rotation is between about 1 and about 200, between about 1 and about 100, between about 1 and about 50, between about 1 and about 20, etc.

In some variations, the OCT imaging sensor is configured to emit energy perpendicular to a longitudinal axis of the catheter device. Thus, the region of the body (including the body lumen) immediately outside of the catheter may be imaged. Because OCT may provides images of structures within the tissue, the tissue forming and surrounding the lumen may be imaged. This information may be used to guide the catheter, and/or to confirm when an occlusion has been reached or crossed.

As mentioned, the rotatable distal tip may comprise a helical blade edge or wedge. In some variations the helical wedge comprises a substantially smooth, curved outer surface that presents an atraumatic tissue-contacting surface when rotated in a first direction (e.g., clockwise) and that further presents a tissue dissection and/or sharp or rough tissue-cutting surface when rotated in an opposite direction to the first direction (e.g., counterclockwise).

In any of the variations described herein one or more imaging markers (e.g., fiducial markers) may be included to help orient, and guide the operation of the device, including positioning the device within the body. A marker may be a radiopaque material (e.g., a metal) that can be seen in high contrast during fluoroscopy) or a material that reflexes or absorbs optical beams from the OCT system (e.g., metal, dense polymer, carbon powder). In variations of the catheter including a fixed jog, the fixed jog may act as a marker, or in conjunction with a marker, to aid in steering the catheter device. In some variations, the elongate body includes at least one marker configured to obstruct imaging from the OCT sensor at least once per rotation of the rotatable tip. More than one marker may also be used (e.g., three markers).

In some variations the device includes a driveshaft that is concentric to the central lumen (e.g., surrounds the central lumen) so that the central lumen extends through the driveshaft. The driveshaft typically rotates the rotatable distal tip.

In general, the imaging sensor may be proximal to (though near) or incorporated within the distal tip. For example, the distal end of the rotatable tip may be less than 3 mm from the imaging sensor.

Also described herein are catheter devices for crossing occlusions, the device comprising: an elongate body; a central lumen extending within the elongate body from a proximal end of the elongate body to a distal end of the elongate body; a rotatable tip having spiral wedges at the distal end of the elongate body and configured to rotate relative to the elongate body; an OCT imaging sensor comprising an optical fiber coupled with the rotatable tip and configured to rotate therewith, wherein the optical fiber is configured to wrap around the central lumen within the elongate body as the rotatable tip rotates; and a drive mechanism configured to continuously rotate the rotatable tip alternately clockwise then counterclockwise.

In another variation, a catheter device for crossing occlusions includes: an elongate body; a central lumen extending within the elongate body from a proximal end of the elongate body to a distal end of the elongate body; a rotatable tip at the distal end of the elongate body and configured to rotate relative to the elongate body; an OCT imaging sensor comprising an optical fiber coupled with the rotatable tip and configured to rotate therewith, wherein the distal end of the elongate body comprises one or more fiduciary markers configured to occlude the OCT imaging sensor as it rotates; and a fixed jog region proximal to the distal end of the catheter, the fixed jog positioning the distal end of the catheter at an angle relative to the region of the catheter proximal to the fixed jog. The fixed jog may form an angle of between about 10 to 45 degrees, so that the distal end is at this angle relative to the region of the elongate body proximal to the fixed jog.

Also described herein are methods of crossing an occlusion or lesion. For example, a method of crossing an occlusion or lesion may include: advancing an occlusion crossing catheter into a body lumen; rotating a rotatable distal tip at a distal end of an elongate body of the occlusion crossing catheter; imaging a region of the body lumen surrounding the catheter using an OCT sensor coupled to the rotatable distal tip; and passing the rotatable distal tip past an occlusion. In some variations a guidewire may be placed after passing the occlusion or lesion, so the method may include the step of advancing a guidewire past the occlusion by passing the guidewire through a central lumen within the elongate body of the occlusion crossing catheter.

In general, the method may include the step of displaying the imaged region surrounding the body lumen on a screen.

Rotating the rotatable tip may include winding an optical fiber forming the OCT sensor around the central lumen of the occlusion crossing catheter. The step of rotating may include alternately rotating the rotatable tip clockwise and then counterclockwise.

In some variations, the entire catheter may also be rotated to orient it within the body lumen. For example, the catheter body may be rotated to orient a fixed jog and steer the catheter towards damaged tissue.

Image correction may be used to enhance the imaging and user interface. For example, in some variations the image may be corrected, modified or enhanced prior (or concurrent with) display. For example, in some variations, the image may be corrected prior to displaying the image data to account for lag of the OCT imaging sensor relative to the detector. The image data may be corrected to mask out portions of the image, including regions of the catheter, noise, and the like. Thus, in some variations the image may be an annular region with the innermost (donut hole) region being shown as blank to represent the catheter diameter, while the outermost region (edge of the annulus) may be masked to remove artifact.

In some variations, the image taken with OCT imaging may be aligned with other imaging means, including fluoroscopic imaging. For example, the method may include the step of orienting image data taken with the OCT sensor to align with a fluoroscopy image.

Also described herein are methods of crossing a chronic total occlusion including the steps of: advancing an occlusion crossing catheter into an occluded body lumen of a patient; rotating a rotatable distal tip of the catheter relative to an elongate body of the catheter, wherein the distal tip includes at least one helical blade and an OCT imaging sensor; imaging a region of the body lumen surrounding the catheter using the OCT sensor on the rotatable tip, wherein the catheter includes at least one marker configured to obstruct imaging form the OCT sensor at least once per rotation of the rotatable tip; and steering the catheter within the body lumen of the patient based upon the OCT image of the body lumen and the marker.

In some variations, the catheter comprises a fixed jog near the rotatable tip having a fixed orientation relative to the at least one marker, and wherein steering comprises rotating the elongate body to orient the fixed jog. The steering can include pointing the distal end of the catheter toward unhealthy tissue imaged by the OCT sensor.

BRIEF DESCRIPTION OF THE DRAWINGS

FIGS. 9A-9C show screen captures used to aid steering an exemplary catheter device.

FIG. 13A shows an end perspective view of the oscillation system of FIGS. 12A and 12B; FIG. 13B-13D illustrate rotation of the camming mechanism and driveshaft of this system.

FIG. 15A shows one variation of an exemplary catheter.

FIG. 15B shows another variation of an exemplary catheter including an inflatable centering feature.

FIG. 19A shows the distal end of the catheter of FIG. 18 fully deflated; FIGS. 19B and 19C show enlarged views of the proximal and distal ends of the deflated balloon of FIG. 18, respectively.

DETAILED DESCRIPTION

Figure 1:
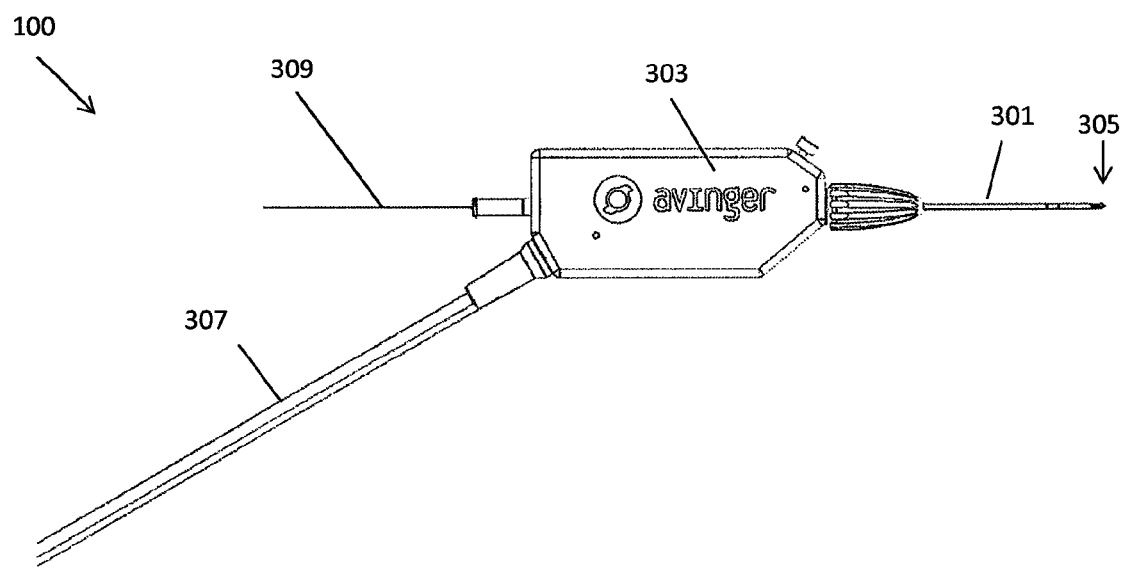
FIG. 1 is a side perspective view of one variation of a catheter device.

The catheters described herein typically include one or more imaging sensors at the distal end that may be rotated independently of the elongate body of a catheter. An imaging sensor may include an optical coherence tomography (OCT) sensor. The rotating distal end may also include one or more tissue cutting or dissecting surfaces that may aid the catheter in advancing within occluded regions of a vessel.

Examples of the types of catheters that are described herein in detail include: (1) guidewire support/placement catheters; (2) support/placement imaging catheters; (3) occlusion crossing catheters (4) occlusion crossing imaging catheters; (5) atherectomy catheters; and (6) atherectomy imaging catheters.

Two sections are included below. Part I describes catheters, including occlusion crossing catheters, that may be used as guidewire placement and support catheters. In particular, Part I describes catheters configured for imaging from the inside of a vessel, such as an artery, during operation. Part II describes atherectomy devices and methods of using them. The sections and subsections provided herein are for convenience only; it should be understood that features included in one section or subsection may be included or excluded from devices described in any of the other sections and subsections.

Part I: Catheters

Catheters, such as occlusion crossing catheters, including guidewire placement and/or support catheters (which may be referred to as "occlusion crossing catheters" for convenience) may be used to cross an occlusion or lesion. These catheters may be used to place a guidewire within an occluded lumen of a vessel. Any of the catheters described herein may include a guidewire lumen spanning all or most of the length of the device and a rotating and/or oscillating (clockwise and/or counterclockwise relative to the long axis of the catheter) distal tip, which may include one or more dissecting (e.g., cutting) surfaces. The rotatable distal tip region may be used to position a catheter through an occluded lumen of a vessel, including for treatment of chronic total occlusions.

Described herein are catheters that include an imaging sensor at the distal tip to allow imaging of the vessel structure and morphology as it is being traversed. Imaging may be forward-facing, lateral-facing, adjustable between forward-facing and lateral-facing, and/or rear-facing or angled between the forward and lateral facing. Any appropriate imaging modality may be used, but particularly those using one or more optical fibers, such as optical coherent tomography ("OCT").

The catheters described herein can be dimensioned to fit within vessels of the body, such as blood vessels. For example, the catheters can be configured to be placed within the peripheral blood vessels. Thus, the catheters can have an outer diameter of less than 0.1 inch, such as less than 0.09 inches, such as less than or equal to 0.08 inches.

In one embodiment, a catheter device includes a distal tip that is rotatable and an onboard imaging system for visualizing the vessel as the device is positioned. In this example, the system includes an OCT imaging system for visualizing the structure and morphology of the vessel walls. The system can see a distance of up to 3 mm, such as up to 2 mm, into the depth of the vessel walls.

Referring to FIG. 1, a catheter (which may be used as a guidewire positioning catheter) 100 includes an elongate flexible shaft 301 and a rotatable distal tip 305 having an imaging sensor, such as an OCT sensor, connected thereto. The shaft 301 extends from a handle region 303 and terminates in the rotatable distal tip 305. The device 100 in FIG. 1 is not necessarily shown to scale, as the length of the shaft has been reduced to show the other features at a more appropriate scale.

A guidewire 309 can extend through the guidewire catheter device 100, such as through a guidewire lumen in the shaft 301. The guidewire 309 may be held resident in the device 100 as it is positioned within a patient or it may be inserted after the distal end of the shaft 301, or at least the distal tip 305, has been positioned within the lumen of the vessel, such as past an occlusion or lesion. The guidewire lumen can be housed inside of a driveshaft (not shown in FIG. 1) configured to rotate the tip 305. Thus, in some variations the driveshaft is a tubular shaft such that the driveshaft may surround the guidewire lumen. In other variations, the driveshaft is a solid shaft which extends through the length of the catheter, and runs alongside (e.g., adjacent to) the guidewire lumen.

The system can include an optical fiber (not shown in FIG. 1) that is fixed at one end to the distal tip 305, but is otherwise free to move around, such as within an internal lumen between a lumen housing the guidewire 309 and an outer casing of the shaft 301. Power and imaging lines 307 ("cabling") may extend from the handle region 303 to connect the optical fiber with a power source and a light source for the OCT system.

The handle region 303 can house the control mechanism for controlling the rotation of the distal tip (and OCT reflector/sensor at the end of the optical fiber). The control mechanism controls the direction of the distal tip as well as the number of revolutions before switching direction. In some embodiments, the handle region 303 can also control the rate of rotation. As discussed further below, the rate of rotation, as well as the number of clockwise and/or counterclockwise rotations, may be optimized to advance the distal end of the device though an otherwise occluded lumen of a vessel while generating a cross sectional image of the lumen, i.e., 360 degrees. The rate and number of rotations may also be optimized to prevent damage to the optical fiber used for the OCT imaging which is attached only at the distal end of the device such that the rest of the fiber can extend along the length of the shaft 301 can wrap, off-axis, around the internal lumen (e.g., guidewire lumen) of the catheter without breaking.

Figure 2A:
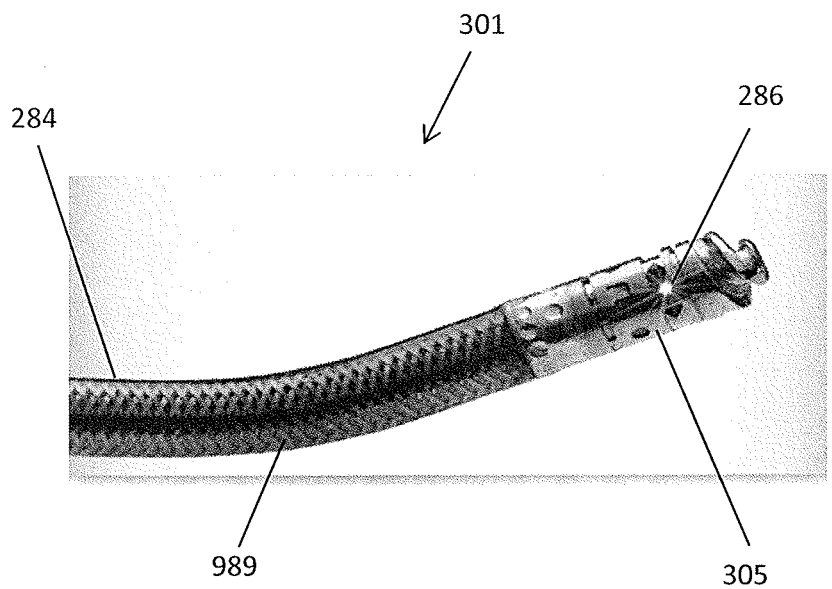
FIG. 2A shows the distal section of an exemplary catheter device.
Figure 2B:
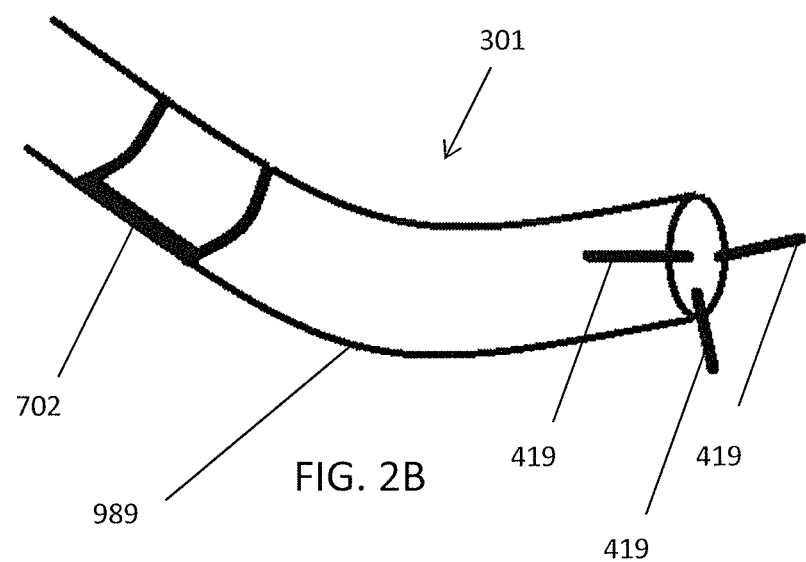
FIG. 2B is a diagram of a distal section of an exemplary catheter device showing the alignment of markers thereon.

Referring to FIGS. 2A and 2B, the shaft 301 can include a fixed jog 989, or a J-shaped bend, near or just proximal to the distal tip 305. The fixed jog 989 can have an angle of 10 to 45 degrees, such as between 20 and 30 degrees. In some embodiments, the jog is shapeable by the user prior to placing the catheter in the body lumen, i.e., the user can fix the jog 989 at the desired angle prior to use. As discussed further below, the fixed jog 989 can aid in steering the shaft 301 to the point of interest. The shaft 301 can include an outer sheath 284. The outer sheath 284 can include a braided material, such as stainless steel, elgiloy, cobalt-chromium alloys, carbon fiber, or Kevlar. The braided material can improve the stiffness of the catheter to help navigate the catheter through vessel. Further, the shaft 301 can include a guidewire lumen 363 (see FIG. 3B) extending within a driveshaft 421 (see FIGS. 3A-3D) from the proximal end to the distal end of the catheter. The guidewire lumen 363 can end in an opening in a distal tip 305 of the device. The guidewire lumen 363 can thus be configured to pass a guidewire therethrough. Further, the distal tip 305 can include an imaging sensor, such as an OCT sensor 286 configured to capture images within a lumen.

Referring to FIGS. 3A-3D, one variation of the distal end of the shaft 301 can have a distal tip 305 that is roughly corkscrew or helically shaped. The distal tip 305 can thus include spiral flutes, such as two spiral flutes. In this variation, the distal tip 305 rotates and does not extend or retract into a housing, i.e. remains exposed from the shaft 301. The distal tip 305 can be attached to a driveshaft 421 that rotates within the outer sheath 284 and can be configured to rotate in both the clockwise and counterclockwise directions. Further, the distal tip 305 can include a substantially smooth, curved outer surface 322 that presents an atraumatic tissue-contacting surface when rotated in one direction, i.e., the counterclockwise direction in FIGS. 3A-3D, and that further presents a sharp, tissue-cutting surface or edge 403 when rotated in the opposite direction, i.e. the clockwise direction in FIGS. 3A-3D.

At least a portion of the tip 305, such as the proximal portion of the tip 305, i.e., the proximal portion of the cutting geometry, can have a diameter that is substantially equal to or greater than the diameter of the shaft 301. That is, the cutting edge 403 can be helical such that at the distal end, the diameter of the cutting geometry is reduced to the size of the guidewire lumen and gradually increases to the approximate outer diameter of the shaft 301 as it moves proximally. Further, the tip 305 can be configured such that it cuts only in the forward direction and not substantially in the lateral direction. That is, the cutting edge 403 can be substantially forward-facing.

An OCT imaging sensor 286 (including the distal end of the optical fiber 411 and the mirror 412) can be fixed to the rotatable distal tip 305 and rotate with it. The distal end of the optical fiber 411 can be secured in a notch 344 formed in the rotatable distal tip 305. An epoxy or other securing material that has a refractive index appropriately mismatched with the end of the optical fiber 411 can hold the end of the optical fiber 411 in the notch 344, as described in U.S. patent application Ser. No. 12/790,703, Publication No. US-2010-0305452-A1, incorporated by reference above. The imaging sensor 286 can direct the optical beam for OCT imaging from the distal tip 305 of the catheter into the tissue. In one embodiment, the imaging system is oriented so that the mirror 412 directs the optical beam approximately or substantially perpendicular to the catheter axis. In some variations, this angle is different or is adjustable. For example, the orientation of the mirror 412 may be changed (including adjusted by the user) to change the direction of imaging and/or image more distally or proximally. As used here, substantially perpendicular may include plus or minus 10 degrees, plus or minus 5 degrees, or plus or minus 2 degrees, off of the 90 degree angle that is perpendicular from the elongate axis of the distal tip and/or catheter body.

The sensor 286 can be located close the distal end of the tip 305, such as just proximal to the cutting edge 403. For example, the sensor 286 can be located within 5 mm of the distal end of the tip 305, such as less than 3 mm, such as approximately 2 mm. Advantageously, by minimizing the distance between the sensor 286 and the distal end of the tip 305, the resulting image will be a closer approximation of the exact tissue or material being passed by the distal end. The sensor 286 may be directed laterally (e.g., to image the sides of the vessel in which the catheter is traveling), or angled forward or backward. The sensor 286 can be located off of the central axis of the shaft 301 and close to the outer diameter of the tip 305, such as within 0.05 inches, e.g. less than 0.3 inches, less than 0.02 inches, or less than or substantially equal to 0.01 inches of the outer diameter of the tip 305. Advantageously, by having the sensor 286 close to the outer diameter, the depth that the OCT system can see into the tissue will be greater, i.e., the amount of tissue lying within the OCT imaging range is increased.

As shown in FIGS. 3A-3E, the rotating tip 305 is held in a chassis 405 that is fixed relative to the shaft 301, i.e., that does not rotate with the rotating tip 305. The chassis 405 is any structure within which the distal tip 305 can rotate and which secures the driveshaft 421 and/or the distal tip 305 to the end of the shaft 301; it may also be referred to as a housing. The outer sheath 284 can be connected to the chassis 405 such that the outer sheath also remains stationary while the distal tip 305 rotates.

Figure 3A:
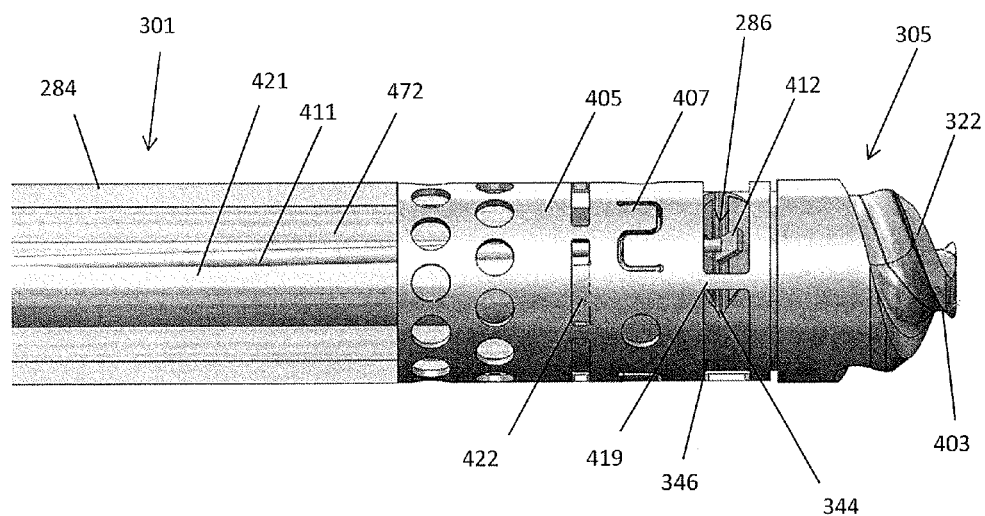
FIGS. 3A-3B show various side perspective views of the distal end an exemplary catheter device.
Figure 3B:
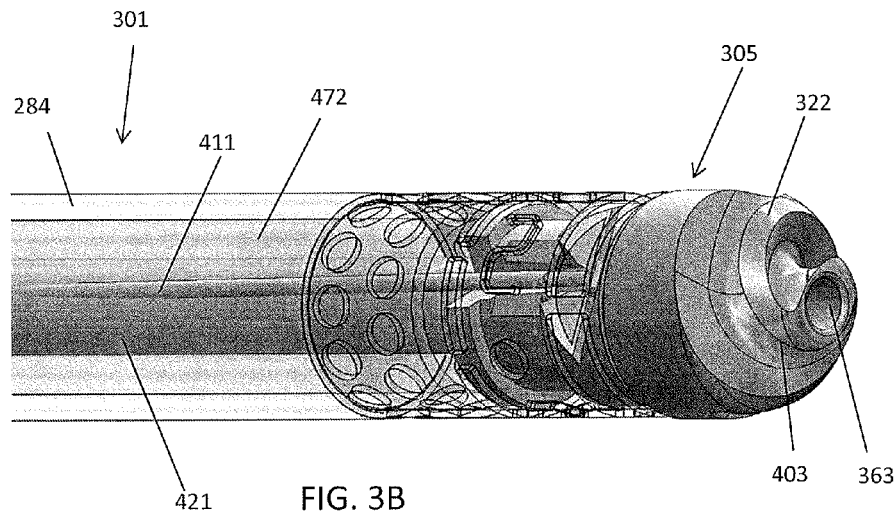

The chassis 405 can have one or more "window" regions through which the OCT imaging sensor 286 can view the tissue. For example, as shown in FIGS. 3A and 3B, the chassis 405 can include three window regions 346 separated by spines 419 (which may be referred to as posts, struts, dividers, separators, etc.) arranged annularly around the chassis 405. These spines 419 may serve as reference markers as the imaging sensor 286 rotates, as discussed below. The spines 419 may be separated from one another by different distances. For example, one of the windows may be larger than the other two, or smaller than the other two. This asymmetric sizing may provide a visual reference on the display of the OCT imaging. Thus, in one example, there are three spines 419 arranged such that there is a 90° window between the first and second spine, a 90° degree window between the second and third spine, and a 180° degree window between the first and third spine. The spines 419 can have a predetermined and fixed location relative to the jog 989 in the catheter. For example, one of the spines 419 can be aligned relative to the jog 989. In one embodiment, shown in FIG. 2B, the second spine 419 is aligned opposite to the jog 989, i.e., such that the catheter points away from the second spine 419 (the inner curved portion of the jog 989 is opposite to the second spine 419 and the outer curved portion of the jog 989 is axially aligned with the second spine 419). This alignment can be used to help orient the device in a specific direction with respect to the image and/or vessel, as discussed further below.

Figure 3C:
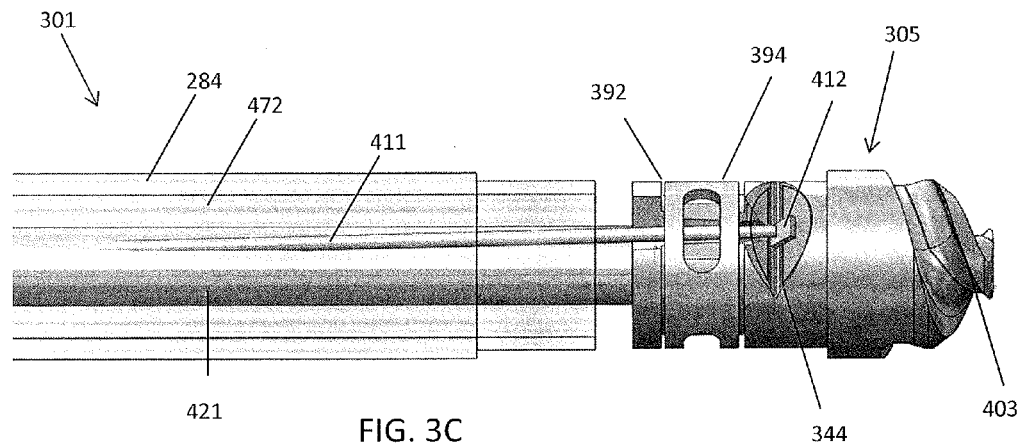
FIG. 3C shows the distal end of the device of FIGS. 3A-3B, but with the collar removed.
Figure 3D:
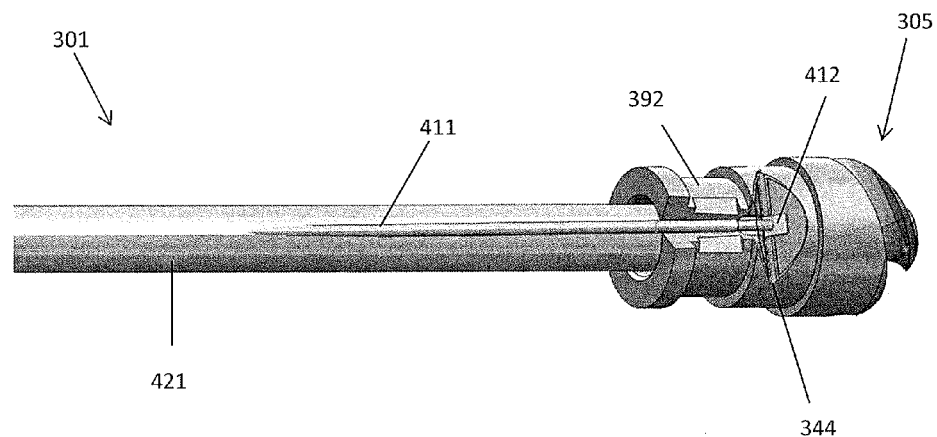
FIG. 3D shows the distal end of the device of FIGS. 3A-3C, but with the collar and outer sheath removed.

As shown in FIGS. 3C-D, the distal tip 305 can include a groove 392 at the proximal end to engage a bushing 394 (e.g., annular ring). The bushing 394 can remain fixed with respect to the shaft 301 and may provide a lubricious surface to eliminate or reduce friction and fix the longitudinal position of the distal tip 305. The bushing 394 may be made of PEEK or other hard lubricous material. In some embodiment, the groove 392 may be crimped or clamped to the stationary chassis 405, thereby allowing the rotatable distal tip 305 to have improved stability during rotation.

Figure 3E:
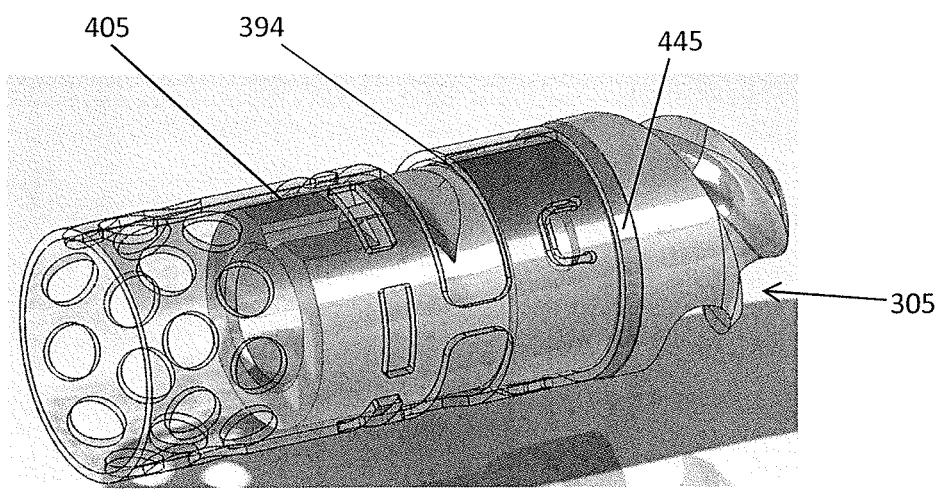
FIG. 3E shows an embodiment of the distal end of an exemplary catheter device wherein the bushing includes a shoulder.

Referring to FIG. 3E, in another embodiment, the bushing 394 includes a shoulder 445. The shoulder 445 can extend outward into the space between the distal edge of the chassis 405 and the distal tip 305. The shoulder 445 can be made of the same lubricous material as the rest of the bushing 394. The shoulder 445 prevents the distal edge of the chassis 405 from rubbing against the tip 305 and further reduces the friction of the system.

As shown in FIG. 3A, the chassis 405 may engage the groove 392 of the distal tip 305 directly, such as by one or more tabs 407 or locks that can be pushed in when the distal tip 905 is held within the chassis 405 to lock the bushing ring 394 and distal tip 305 in position. The chassis 405 or distal tip 305 can be made from a lubricious material.

Referring to FIGS. 3A-B, the chassis 405 can include one or more openings or ports 422 out of which a clearing fluid, such as saline or water, may be driven to help clear the pathway for imaging the walls of the vessel lumen as the device is operated. Blood, including red blood cells and other blood components, may degrade the ability of the OCT imaging system from imaging other tissues because OCT may not readily "see" through blood. Thus, the catheter may be configured to clear the blood from the region of interest, i.e., the region where the optical beam is emitted from the catheter for OCT imaging. The ports 422 can thus be configured to emit a clearing fluid from the catheter to clear blood from the imaging sensor. Thus, in this variation the port 422 is located directly adjacent to the imaging sensor and emits fluid to clear blood from the region where the optical beam is being emitted. The ports 422 can be less than 2 mm from the imaging sensor, such as less than 1.5 mm. Advantageously, by having the ports 422 close to the imaging sensor, the pressure and amount of clearing fluid required to clear the blood from the region of interest can be low. For example, less than 1 ml, such as less than 0.5 ml, e.g., less than 0.2 ml of clearing fluid can be required to clear the blood from the region of interest. Thus, the required pressure may be nominal and the flow of saline or other clearing fluid may be minimal and still effectively clear blood from the imaging space, greatly improving the resolution of the vessel walls and increasing the depth of penetration. Further, using small amounts of clearing fluid can advantageously avoid problems associated with having too much fluid in a small space, such as separation of tissue (e.g., dissection).

The shaft 301 can be configured such that the clearing fluid enters at the proximal end of the catheter and is transported to the distal end by flowing in a space 472 between the outer sheath 284 and the driveshaft 421. The clearing fluid may be pressurized from the proximal end (e.g., using a syringe, etc.) so that it is pushed out of the opening 422 to clear blood from the OCT pathway.

Figure 4:
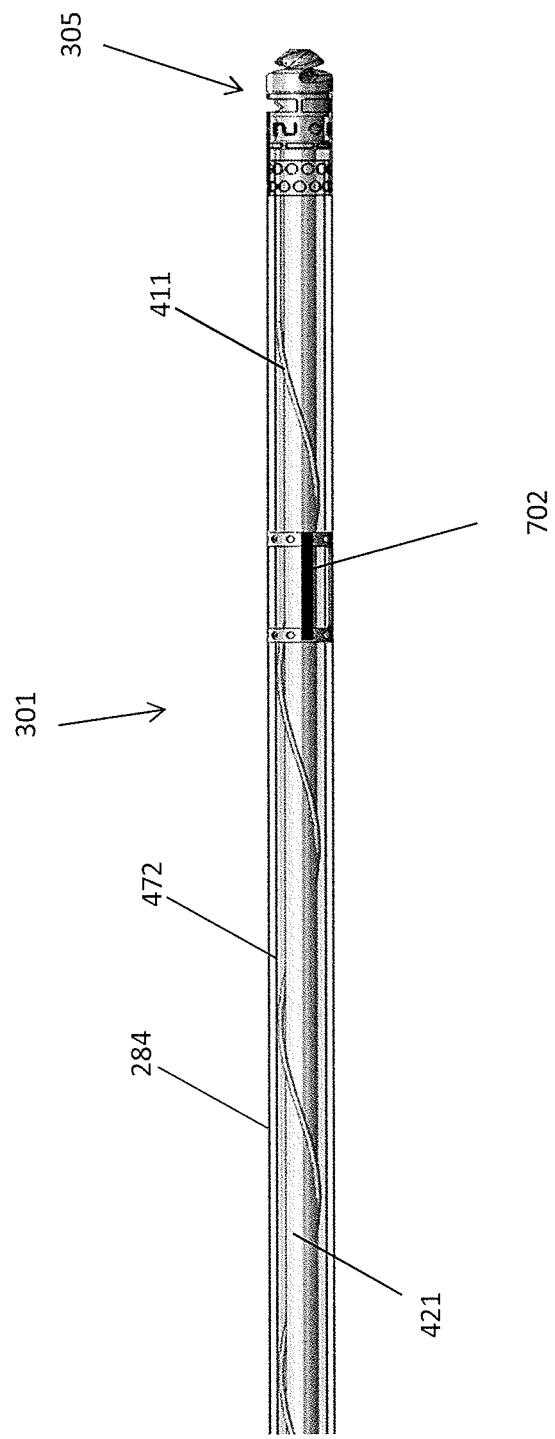
FIG. 4 shows an optical fiber wrapped around a driveshaft of an exemplary catheter device.

Referring to FIG. 4, the OCT portion of the catheter device 100 may be referred to as an off-axis imaging system because the management of the OCT optical fiber 411 is arranged asymmetrically, off-axis with reference to the long axis of the catheter. The fiber 411 can be configured to extend freely within the shaft 301 in the space 472 between the driveshaft 421 and the outer sheath 284 except where it is attached at the distal end of the device, e.g., at the rotatable distal tip 305. Accordingly, as shown in FIG. 4, when the driveshaft 421 is rotated to rotate the distal tip 305, the fiber 411 can wrap around the driveshaft 421. This arrangement can advantageously enhance the flexibility, i.e., allow for movement of the catheter without fracturing the optical fiber 411.

Because the optical fiber 411 winds and unwinds around the driveshaft 421 as it is rotated with the distal tip 305, both the rate of rotation and the number of rotations may be controlled to optimize performance, prevent the fiber 411 from binding within the shaft 301, and prevent the fiber 411 from snapping due to excessive twisting or rotation. For example, the distal tip 305 may be configured to alternate its rotation from clockwise to counter clockwise. Thus, the driveshaft 421 can be configured to rotate (with the distal tip 305) clockwise for a fixed number of rotations and to rotate counterclockwise for the same number of rotation before switching back to clockwise rotations and repeating the process. The number of rotations in the clockwise direction can be substantially equivalent to the number of counter clockwise rotations in order to relieve any residual twisting. Advantageously, by having a substantially equivalent number of rotations in the clockwise and counterclockwise directions, accumulation of fiber twisting can be avoided, thereby avoiding snapping of the fiber due to such accumulated twisting. In general, the device is configured to rotate the distal tip n rotations clockwise and n rotations counterclockwise, switching between clockwise and counterclockwise rotational direction after each n rotations. The number of rotations n can be any number, including fractional, typically between 1 and 100; preferably it is between 1 and 10, depending on the length of the catheter and the amount of stress the fiber can withstand. For example, the device may be configured to rotate approximately 6, 8.5, 10, 12.7, 15, etc. times clockwise, then counterclockwise the same number of rotations. Thus, the device is configured so that it doesn't continuously spin clockwise or counterclockwise, but has a limited number of rotations in either direction (e.g., less than 25 rotations, such as 10 rotations), after which it automatically switches to rotate the other direction. The transition between clockwise and counterclockwise rotation may be performed automatically, which is described in more detail with reference to FIGS. 5A-5E, below.

The rotation may be driven by a motor or other driver (e.g., within the handle) or it may be manual. Preferably, the rotation is automatic, and is driven at a constant speed that is typically between about 1 and 300 revolutions per minute (rpm); for example, the rotation rate may be about 10 rpm, 20 rpm, 30 rpm, 40 rpm, 50 rpm, 60 rpm, etc. In some variations, the distal tip is rotated between about 1 and about 100 rpm, e.g., between about 1 and 80 rpm, such as between about 30 and 60 rpm. The rate and the consistency of rotation may be optimized for penetration through the occlusion within the vessel, for image stability, and also to produce relatively streak-free imaging using the OCT. Thus, the rate of rotation may be limited to an upper limit speed that is held relatively constant. In addition, the rate of rotation may be sufficiently low (e.g., less than 150 or 100 or 50 rpm) so that the distal head rotates but does not 'drill' through the tissue, including one or more occlusions. In some embodiments, the user can control the rate of rotation, such as by setting the motor to rotate at a particular speed.

Referring to FIG. 5A-5E, the handle 303 of the device can be configured to control rotation and advancement of the shaft 301. The handle 303 can include a switch 562 configured to turn the system on or off (i.e. to start the rotation of the distal tip and/or the imaging system). The handle can be covered by a housing 501 which may be configured to conform to a hand or may be configured to lock into a holder (e.g., for connection to a positioning arm, a bed or gurney, etc.). Within the handle 303, a drive system, including a motor 503 and drive gears 515, 516, 517, may drive the driveshaft 421 to rotate the distal tip 305 of the device and/or the OCT imaging system relative to the shaft 301. In some variations, the drive system is controlled or regulated by a toggling/directional control subsystem for switching the direction of rotation of the driveshaft between the clockwise and counterclockwise direction for a predetermined number of rotations (e.g., 10).

In FIGS. 5A-5E, a mechanical directional control can be configured to switch the direction of rotation between clockwise and counterclockwise when the predetermined number of rotations have been completed. In this example, the directional control includes a threaded track (or screw) 511 which rotates to drive a nut 513 in linear motion; rotation of the threaded track by the motor 503 results in linear motion of the nut along the rotating (but longitudinally fixed) threaded track 511. As the motor 503 powers the driveshaft 421 in a first rotational direction (e.g., clockwise), the nut 513 moves linearly in a first linear direction (e.g., forward) until it hits one arm of a U-shaped toggle switch 516, driving the U-shaped toggle switch in the first linear direction and flipping a switch 523 (visible in FIG. 5D) to change the direction of the motor 503 to a second rotational direction (e.g., counterclockwise), and causing the nut to move linearly in a second linear direction (e.g., backward) until it hits the opposite side of the U-shape toggle switch 516, triggering the switch to again change the direction of rotation back to the first rotational direction (e.g., clockwise). This process may be repeated continuously as the motor is rotated. The motor 503 may be configured to rotate the driveshaft 421 in either direction at a constant speed. The system may also include additional elements (e.g., signal conditioners, electrical control elements, etc.) to regulate the motor as it switches direction.

The number of threads and/or length of the threaded track (screw) 511 may determine the number of rotations that are made by the system between changes in rotational direction. For example, the number of rotations may be adjusted by changing the width of the U-shaped toggle 514 (e.g., the spacing between the arms). Lengthening the arms (or increasing the pitch of the screw) would increase the number of rotational turns between changes in direction (n). The toggle may therefore slide from side-to-side in order to switch the direction of the motor. The length of the nut 513 can also determine the number of rotations that are made by the system between changes in rotational direction, i.e., the longer the nut, the fewer the number of rotations before switching direction.

In some variations, the motor 503 is rotated in a constant direction, and the switch between clockwise and counterclockwise is achieved by switching between gearing systems, engaging and disengaging an additional gear, or using gears that mechanically change the direction that the driveshaft is driven.

In the exemplary device shown in FIGS. 5A to 5E, the drive system includes the motor and three gears that engage each other to drive the driveshaft in rotation. For example, the motor 503 rotates a first gear 517, which is engaged with a second gear 516 (shown in this example as a 1:1 gearing, although any other gear ratio may be used, as appropriate).

A third gear 515 engages with the second gear 516. The third gear may drive or regulate an encoder 507 for encoding the rotational motion. This encoded information may in turn be used by the drive system, providing feedback to the drive system, or may be provided to the imaging system.

Figure 5A:
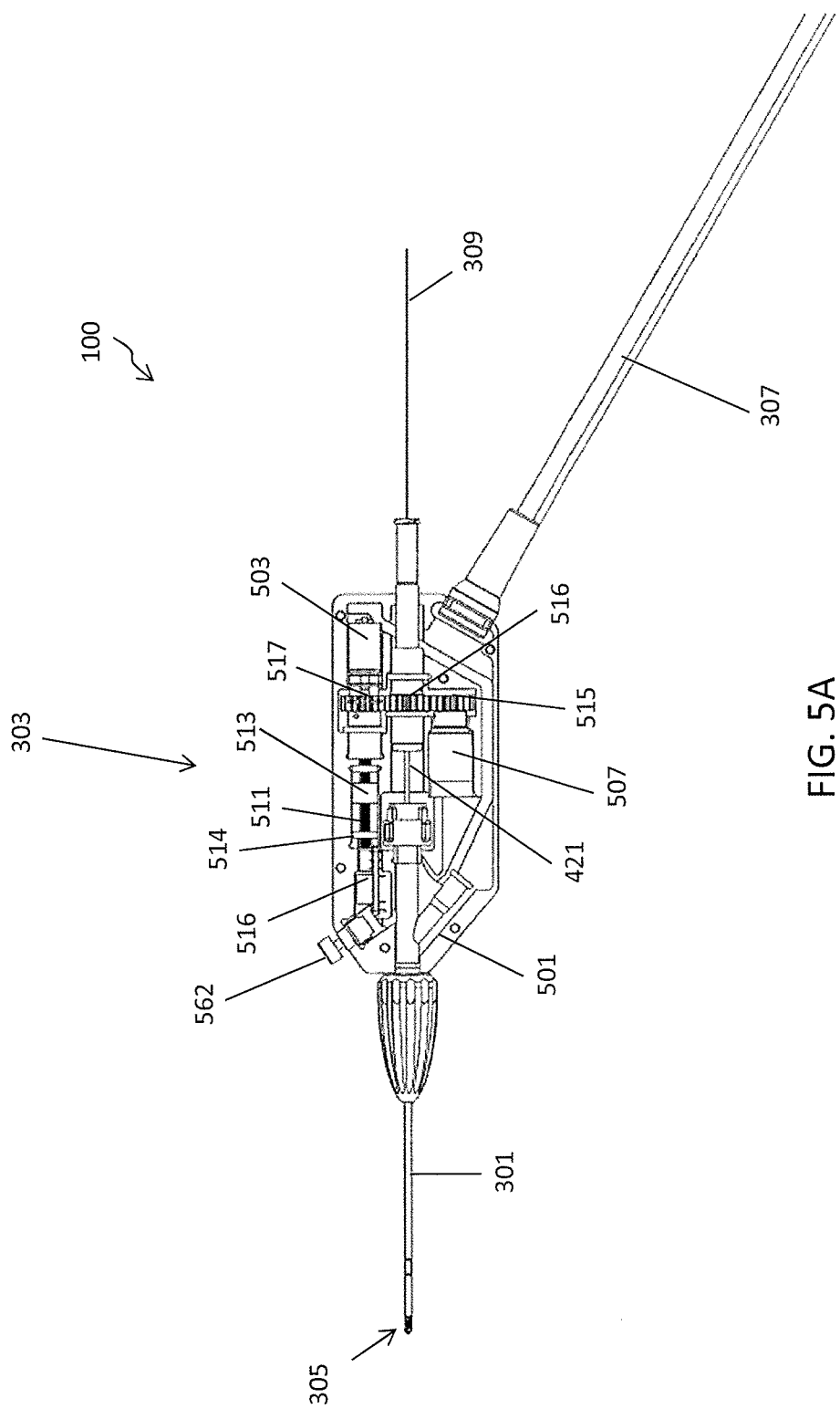
FIGS. 5A-5E show a handle assembly or partial handle assembly for an exemplary catheter device.
Figure 5B:
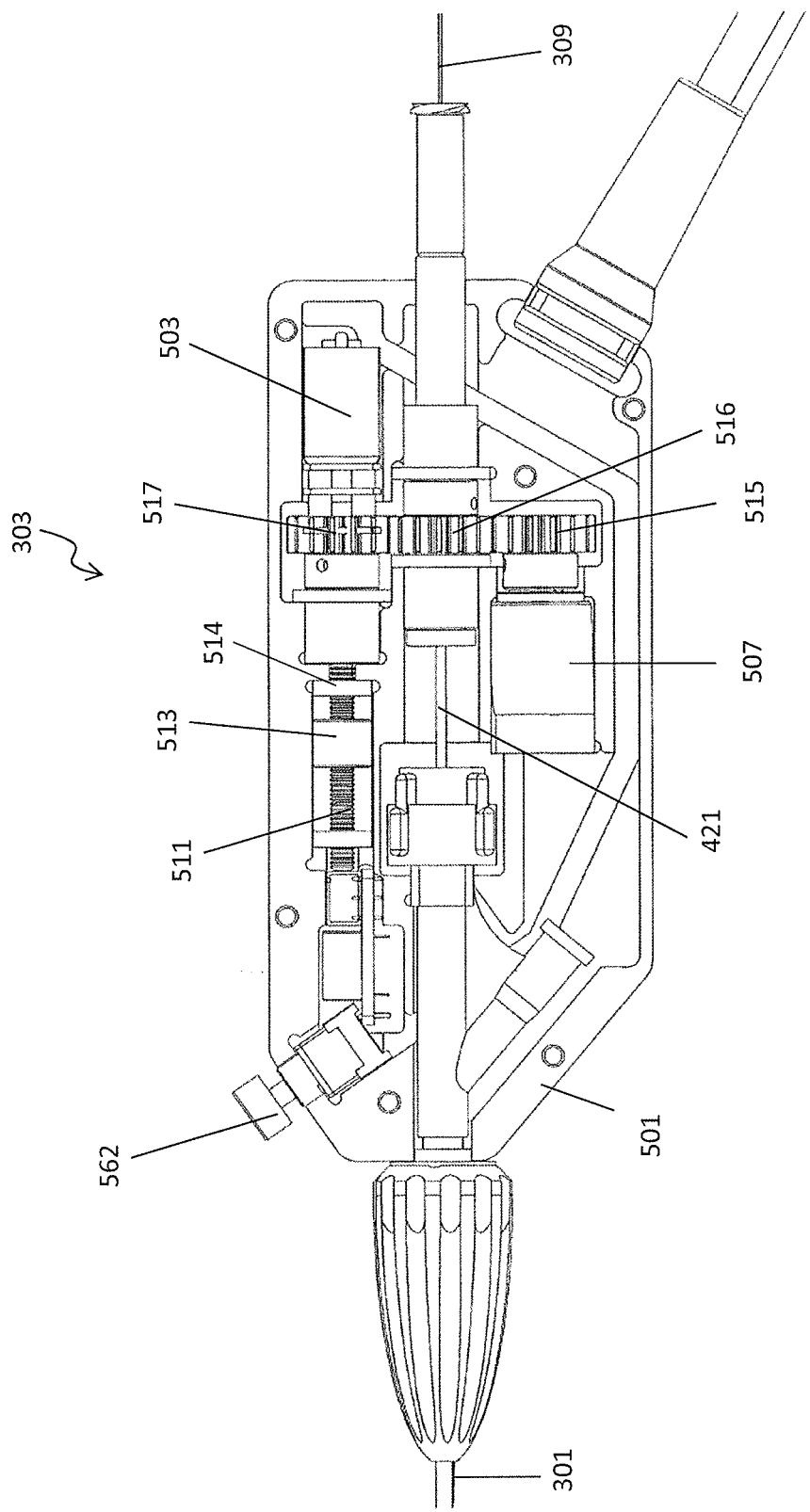
Figure 5C:
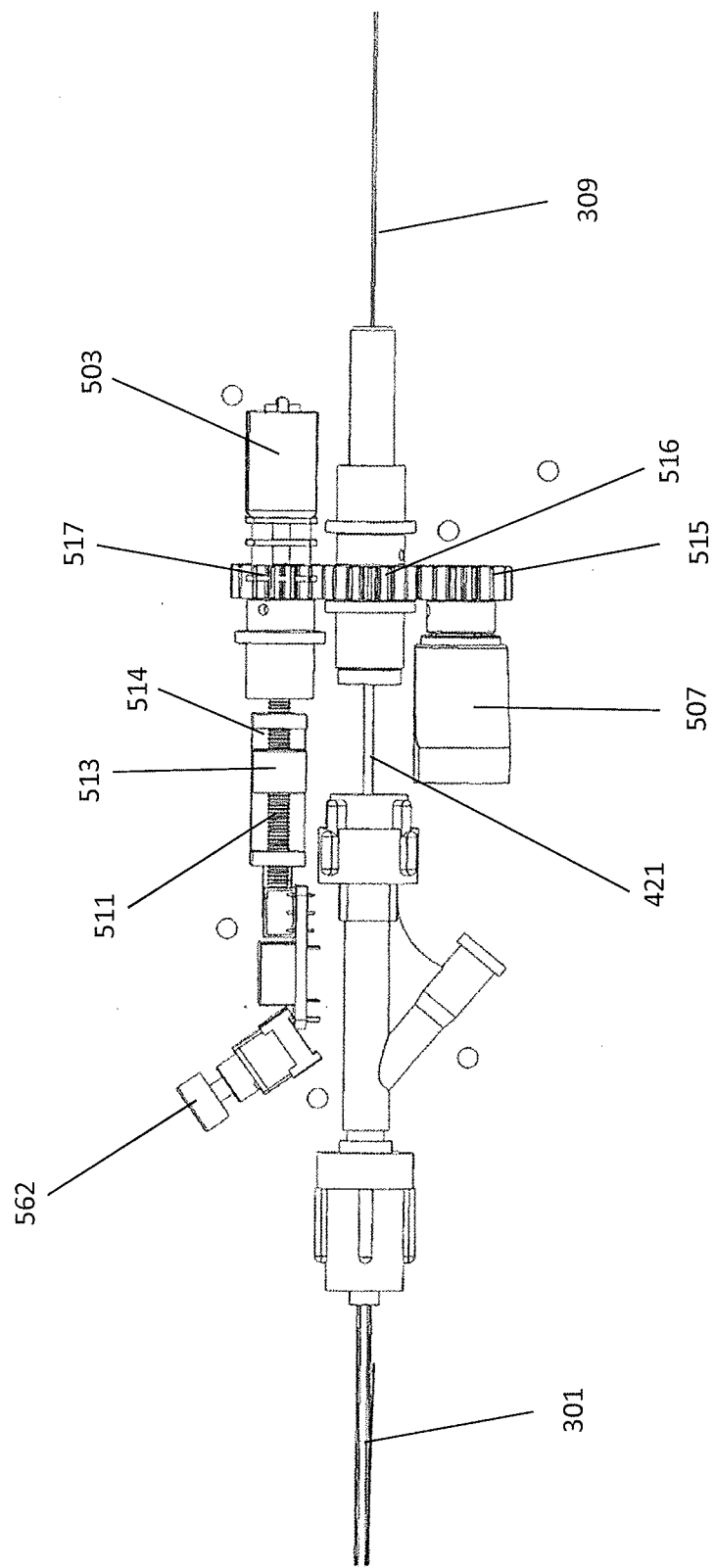
Figure 5D:
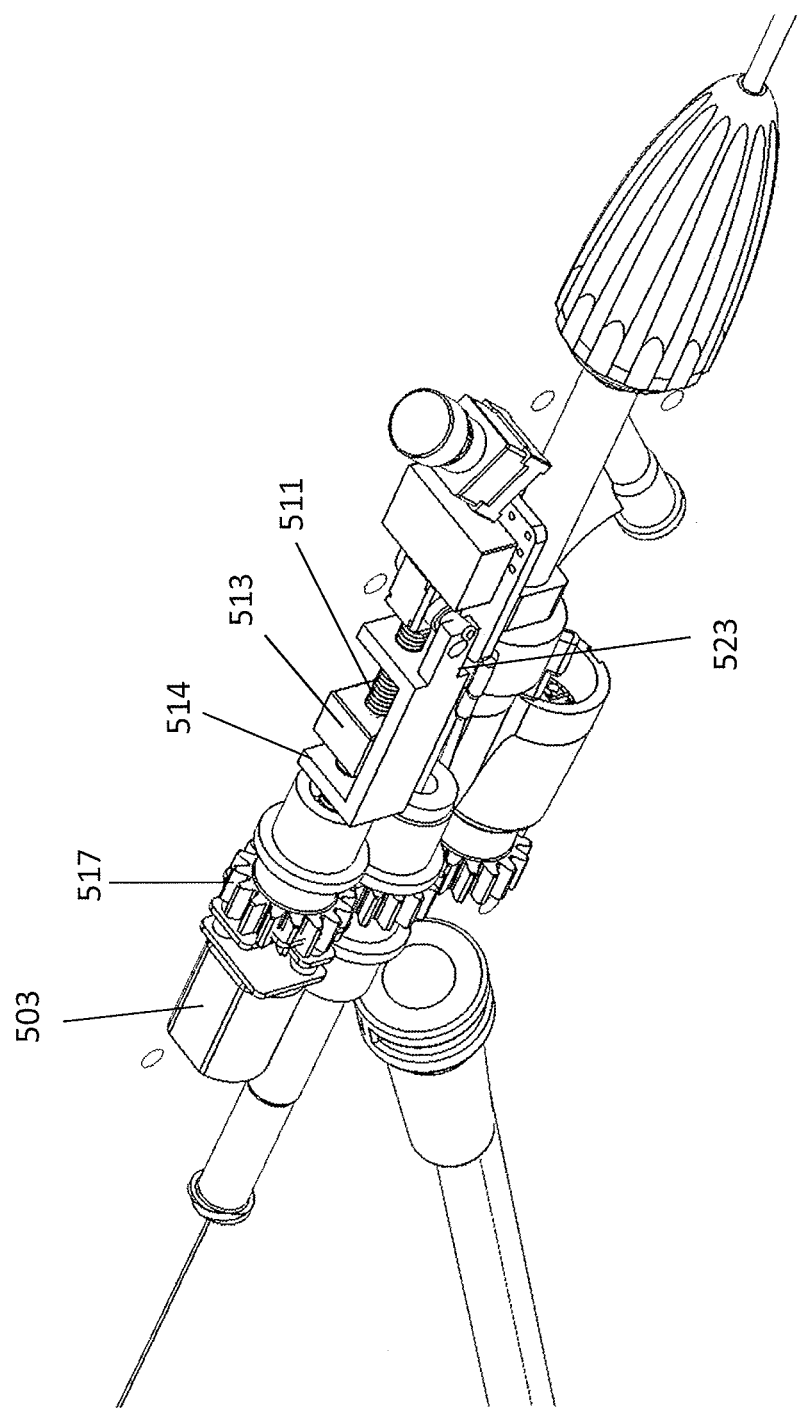
Figure 5E:
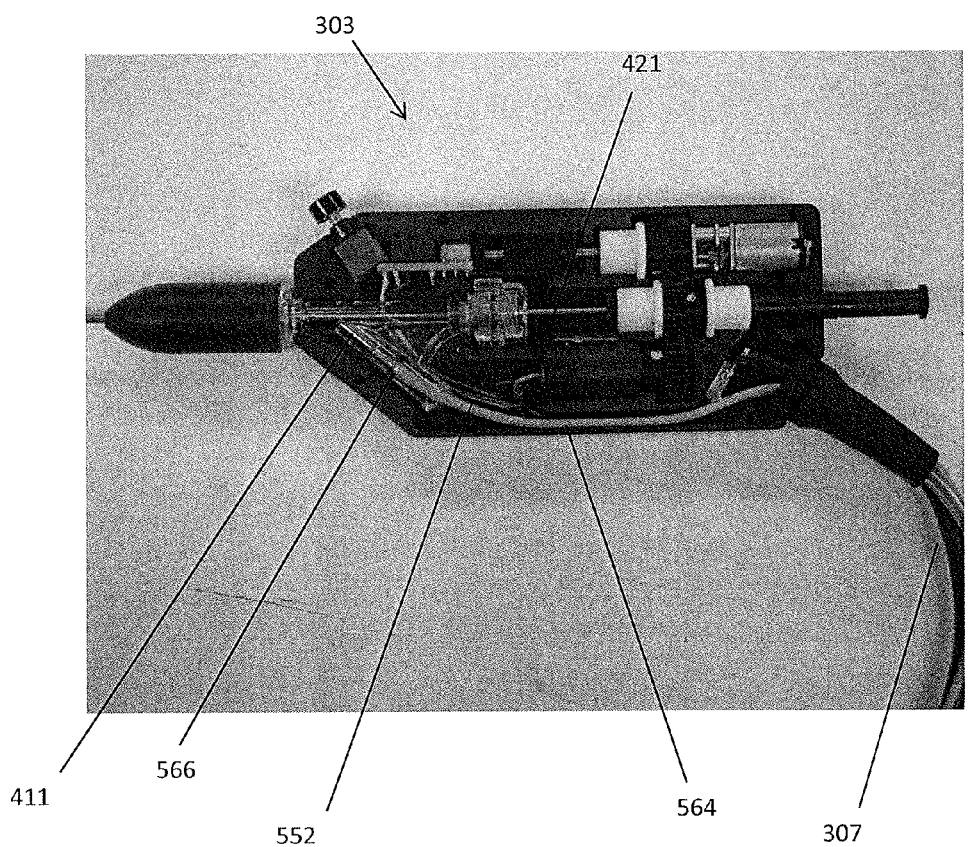

Referring to FIG. 5E, the cabling 307 can include both a fluid flush line 552 configured to be attached to a fluid source and an optical fiber 411 configured to be connected to the OCT system. The flush line 552 and the fiber 411 can both run through the handle 303. The fiber 411 and the flush line 552 can be bonded at a bonding point 566 in the handle 303, creating a seal to prevent fluid from leaking into the handle. The flush line 552 can end at the bonding point 566, allowing the fluid to exit the flush line and continue down the shaft 301 in the space 572 between the outer sheath 284 and the driveshaft 421. Further, the fiber 411 can extend through the bonding point 566 and wrap around the driveshaft 421 in the space 572. As shown, because the fiber 411 is configured to wrap around the guidewire lumen, a separate fiber management system is not necessary. In some embodiments, a protective coating 564 can surround the optical fiber until distal of the bonding point 566.

Figure 6:
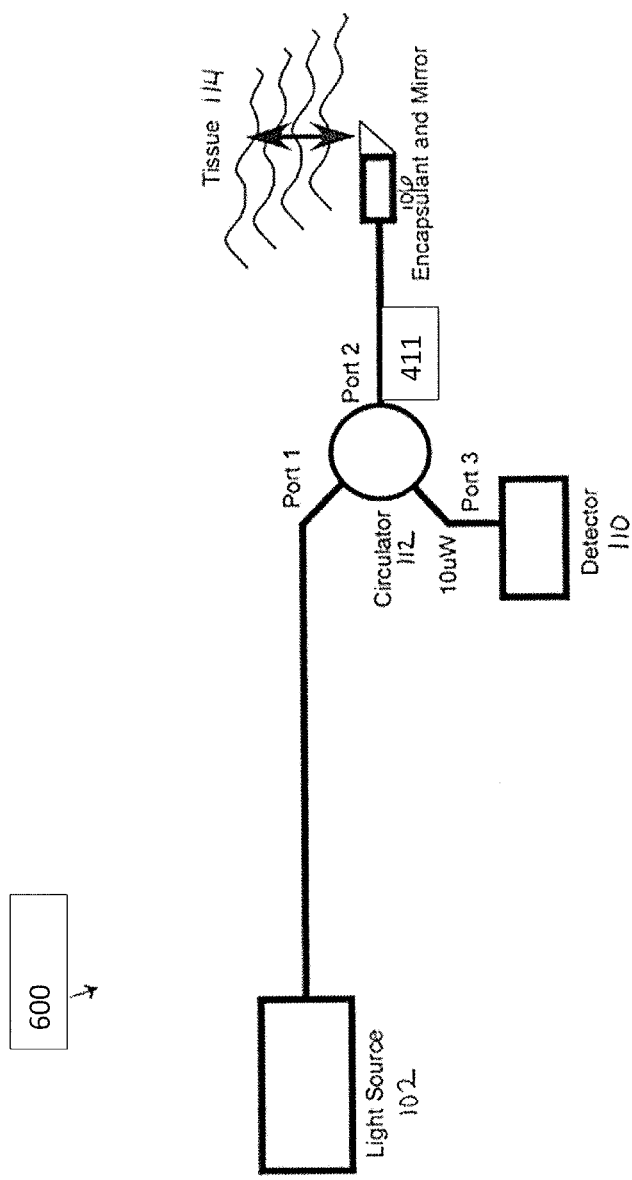
FIG. 6 shows an exemplary OCT system.

Referring to FIG. 6, the fiber 411 can be connected at the proximal end to a common-path OCT system 600. The common-path OCT system 600 includes a light source 102, such as a swept frequency laser. In an alternative arrangement, the light source could be a broadband light source such as a super-luminescent diode (to conduct Time Domain OCT or Spectral Domain OCT using an optical spectrometer). The optical fiber 411 transfers radiation from the light source 102 to the target 114. The optical fiber 411 is in optical contact with an interface medium 106, i.e. the light exiting the optical fiber and entering the interface medium sees only one interface. In some embodiments, as shown in FIG. 6, the end of the optical fiber is embedded in the interface medium 106. The interface medium 106 can be, for example, a glue or epoxy. In the common-path OCT system 600, the index of refraction of the interface medium 106 is different than the index of refraction of the core of the optical fiber 411. This creates a Fresnel reflection, in which part of the light exits the core, and part of the light is reflected back. Some of the light beam that exits the optical fiber 411 will encounter the target 114 and be reflected or scattered by the target 114. Some of this reflected or scattered light will, in turn, reenter the tip of the optical fiber 411 and travel back down the fiber 411 in the opposite direction. A Faraday isolation device 112, such as a Faraday Effect optical circulator, can be used to separate the paths of the outgoing light source signal and the target and reference signals returning from the distal end of the fiber. The reflected or scattered target light and the Fresnel-reflected reference light from the fiber face can travel back to a detector 110 located at the proximal end of the optical fiber 411.

Because the reflected or scattered target light in the OCT system 600 travels a longer distance than the Fresnel reflected reference light, the reflected or scattered target light can be displaced by frequency, phase and or time with respect to the reference beam. For example, if swept-source radiation is used, then the light from the target will be displaced in frequency. The difference in displacement in phase, time or frequency between the reflected or scattered target light and the reference light can be used to derive the path length difference between the end of the optical fiber tip and the light reflecting or light scattering region of the target. In the case of swept source OCT, the displacement is encoded as a beat frequency heterodyned on the carrier reference beam.

The light source 102 can operate at a wavelength within the biological window where both hemoglobin and water do not strongly absorb the light, i.e. between 800 nm and 1.4 µm. For example, the light source 102 can operate at a center wavelength of between about 1300 nm and 1400 nm, such as about 1310 nm to 1340 nm. The optical fiber 411 can be a single mode optical fiber for the ranges of wavelengths provided by the light source 102.

Figure 7A:
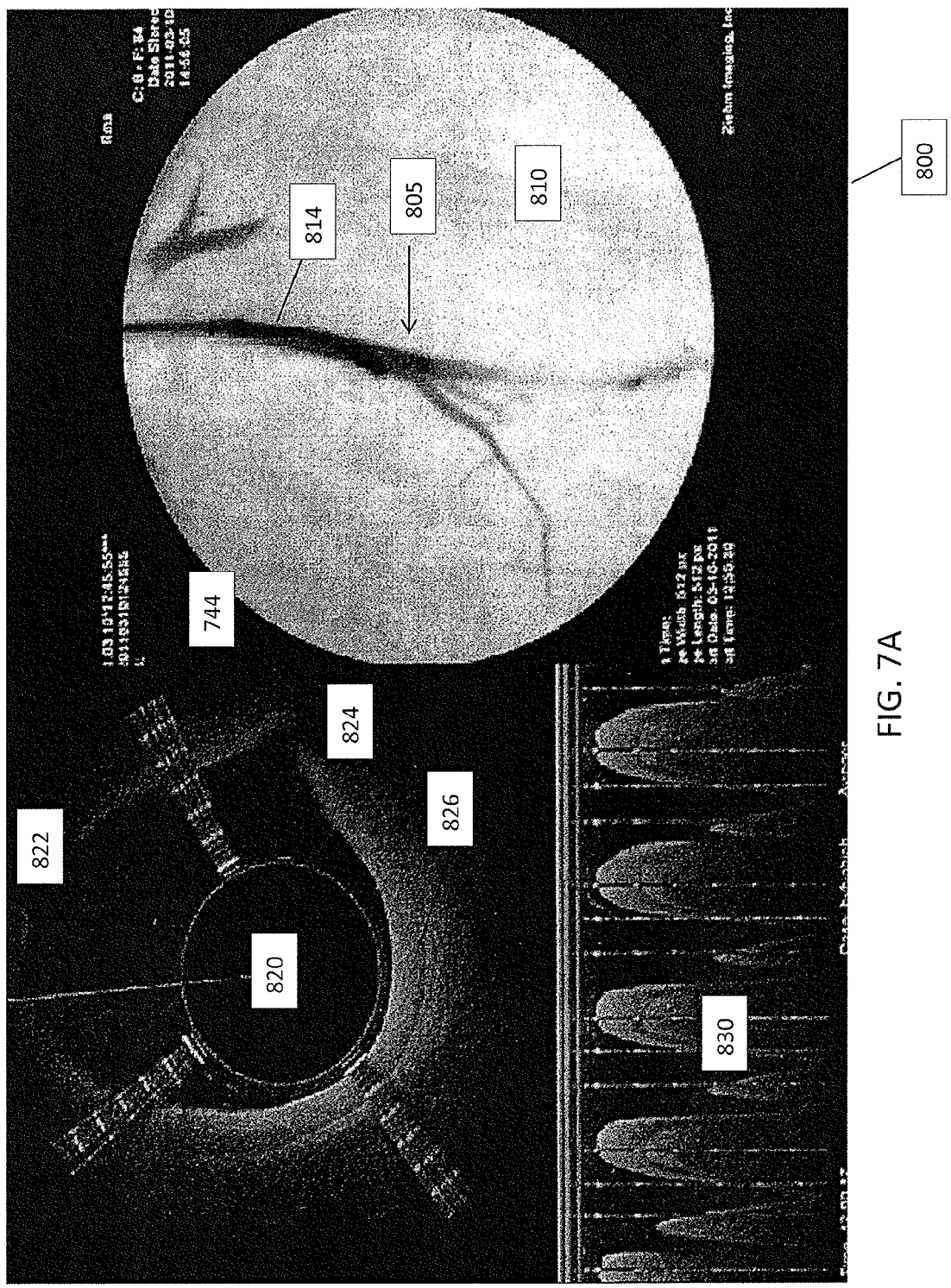
FIGS. 7A and 7B show screen captures of an exemplary catheter device including an OCT imaging system.
Figure 7B:
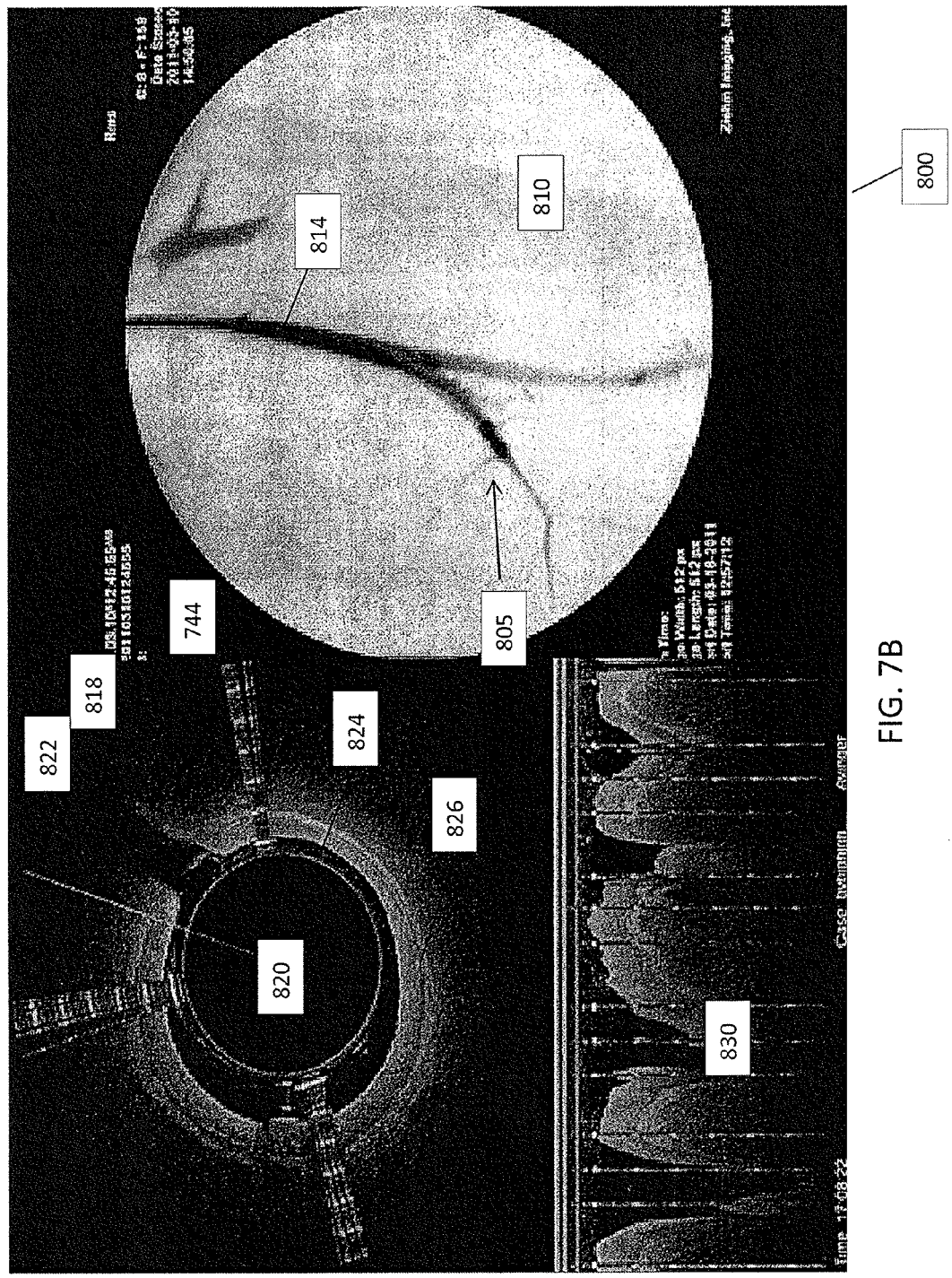

FIGS. 7A and 7B are exemplary screen captures of an imaging output from the system described herein. In FIGS. 7A and 7B, the displayed image 800 is divided into three components. On the right is a fluoroscopic image 810 showing the distal end 805 of the catheter within a vessel 814. Contrast has been inserted into the vessel 814 to show the extent of the vessel 814 and any occluded regions.

On the left is an OCT image 820. To obtain the OCT image 820, the distal tip of the catheter rotates at approximately 30 rpm, and the OCT system provides a continuous set of images as the catheter rotates within the vessel. The images are combined into a continuously updated OCT image 820 that corresponds to the inside of the lumen in which the catheter is inserted. That is, the OCT image 820 is an image trace of the interior of the vessel just proximal to the distal tip as it rotates. The line 822 (extending to almost 12 o'clock in the figure) indicates the current direction of the OCT laser beam as it is rotating. The circle 824 in the middle of the image 820 represents the diameter of the catheter, and thus the area surrounding the circle 824 indicates the vessel. The OCT imaging can extend more than 1 mm from the imaging sensor, such as approximately 2 mm or approximately 3 mm and thus will extend into the walls of the vessel (particularly in the closer region of the vessel) so that the different layers 826 of the vessel may be imaged. In this figure, the three striped rays 744 (extending at approximately 2 o'clock, between 7 and 8 o'clock, and approximately 11 o'clock) indicate the location of the three spines of the catheter and thus may act as directional markers, indicating the orientation of the distal end of the catheter within the body. As described in more detail below, the user may also be able to determine relative orientation of the OCT image (relative to the patient's body orientation) using these striped rays 744.

On the bottom left of the image 800 is a waterfall view 830 of the OCT image as it circles the radius of the body. This waterfall image 830 may be particularly useful in some applications of the system, for example, indicating the relative longitudinal position of a feature (e.g., layered structures, occlusions, branching region, etc.) as the device is moved longitudinally within the vessel. The waterfall view 830 typically includes a time axis (the x-axis) while the y-axis shows the image from the OCT sensor. In addition, the waterfall view 830 may provide an indication of when the catheter has crossed an occlusion. For example, the waterfall view 830 may show the patient's heartbeat when the walls of the vessel move relative to the heartbeat. In these cases, the waterfall view 830 may show the walls of the vessel moving with the heartbeat. In contrast, when the distal tip is within an occlusion the wall of the vessel, the waterfall view will not show movement of the walls since the occlusion material typically prevents the movement of the walls due to the heartbeat, while in healthy vessels the heartbeat is apparent. Thus it may be possible to determine when the catheter has crossed the occlusion based on the waterfall view 830. In some variations, this effect may be automated to provide an indication of when the device is within or has crossed an occlusion. In general, crossing the boundary of a total occlusion is not well defined and may result in inadvertently dissecting the vessel. When the catheter is within the true lumen, the vessel wall may move; if the catheter tip is not in the true lumen all or part of the vessel wall will not move. Thus, this movement of the wall during heartbeat may reflect the position within the true versus false lumen.

FIG. 7B shows another screen capture from the same procedure shown in FIG. 7A. As shown in the fluoroscopy image 810, the distal tip 305 is further within the vessel 814 than in FIG. 7B. In this example, the OCT image 820 shows a branch 818 of the vessel extending from the vessel in the 2 o'clock position.

Figure 8:
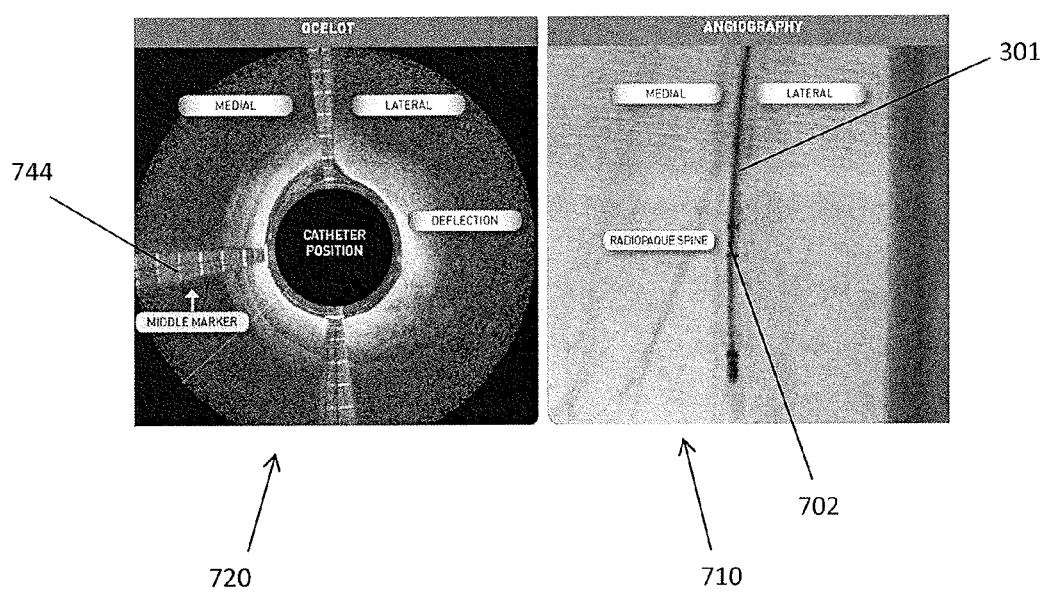
FIG. 8 shows the orientation of an OCT image relative to a fluoroscopy image from a catheter device.

The generated fluoroscopy images and OCT images can be oriented relative to one another, e.g., so that what the user sees on the right side of the OCT image is consistent with what the user sees on the right side of the fluoroscopy image. Referring to FIG. 8, the shaft 301 can include a fluoroscopy marker 702 (also shown in FIG. 2B and FIG. 4) that provides varying contrast in a fluoroscopy image depending on its radial orientation. The marker may be a radiopaque band with one or more asymmetric features such as a "C", "T", or dog bone shape that can be used to radially orient the shaft because the fluoroscopic image of the marker will change depending on its orientation. The fluoroscopy marker 702 can have a fixed location relative to the spines 419 and/or the jog 989. For example, as shown in FIG. 2B, the fluoroscopy marker 702 can be aligned opposite to the jog 989 and/or axially aligned with the second spine 419 described above. The fluoroscopy marker 702 can be used to align a fluoroscopy image 710 with an OCT image 720 during use of the catheter.

As shown in FIG. 8, to align the fluoroscopy image 710 with the OCT image 720, the shaft 301 can be rotated slightly such that the marker 702 is aligned to a particular side of the screen, such as at the 9 o'clock position. The up/down position of the catheter (i.e. whether the catheter is pointed down, as shown in FIG. 7, or pointed up) can also be determined. After the rotational position and the up/down position of the catheter have been determined using the fluoroscopy image 710, the OCT image can then be oriented such that striped ray 744 from the middle marker (the second spine 419 described above) of the shaft 301 is also at the 9 o'clock position in the OCT image 720. Such positioning can be termed "fluorosyncing." Fluorosyncing can be performed using manual input from the user, such as information regarding the up/down position and the rotational position, or can be performed automatically. To orient the OCT image 720 using this information, the software may draw the OCT image 720 either in a clockwise or counterclockwise direction (depending on the up/down orientation of the catheter in the fluoroscopy image 710) and will rotate the image 90°, 180°, or 270° (depending on the rotational position of the catheter in the fluoroscopy image 710).

Once the fluorosync has been completed, the absolute and relative position and orientation of the catheter within the patient's body may be determined. The markers on the chassis/imaging system (visible in the OCT system) may therefore provide sufficient orientation markers such that the fluoroscopic imaging may be reduced.

The displayed images can be used, in combination with steering mechanisms such as the OCT markers, the fluoroscopy marker, and the fixed jog of the device, to steer the catheter and rotatable tip to the desired location. Referring to FIG. 9A, the OCT image 920 shows healthy tissue 956 in the form of a layered structure and non-healthy tissue 958 in the form of a nonlayered structure. The cat ears 962 in the image show a region between the healthy and unhealthy tissue caused by a slight expansion of the vessel around the catheter at that location. Accordingly, during a CTO procedure, one goal may be to steer the catheter towards the unhealthy tissue. Because the middle spine 419 is aligned opposite to the jog 989 (as shown in FIG. 2B), the ray 744 corresponding to the middle spine 419 can be oriented opposite to the non-healthy tissue 958 to steer the catheter in the correct direction. FIG. 9B shows the catheter deflected toward the layered, healthy tissue. FIG. 9C shows the catheter rotated such that it is deflected toward the unhealthy, non-layered structure. Thus, the system may be configured to allow the orientation of the catheter to be rotated into the correct position using the fixed directional markers from the chassis that are visualized by the OCT. In some variations, the distal end of the device may be steerable and may be steered while still rotating the distal end of the device.

Additional steering members may also be included, such as a selective stiffening member, which may be withdrawn/inserted to help steer the device, and/or one or more tendon members to bend/extend the device for steering.

Figure 10:
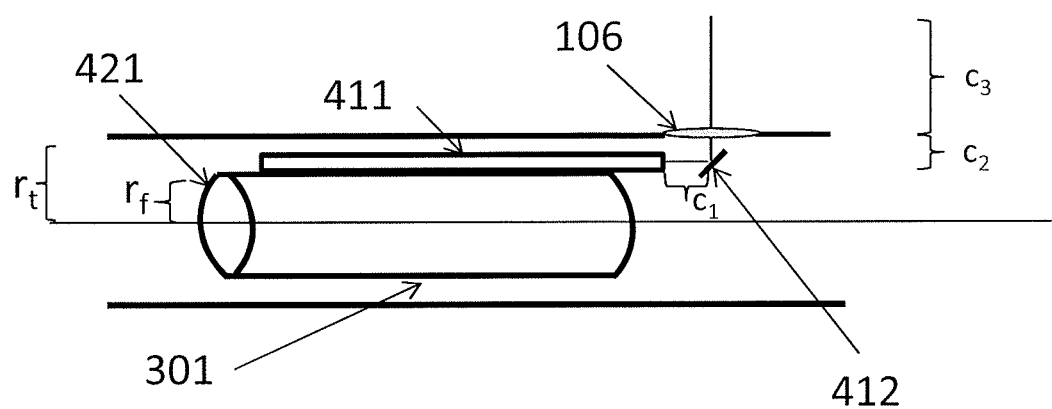
FIG. 10 shows an exemplary diagram used to determine the amount of central masking required for an OCT image of an exemplary catheter device.

Image correction can be performed on the resulting OCT images in order to mask out unwanted or unnecessary portions of the image. For example, referring to FIG. 10, the fiber 411 can be configured such that it ends within the shaft 301. As a result, the fiber 411 will image the distance $c1$ between the fiber 411 distal end and the mirror 412 as well as the axial distance $c2$ between the mirror 412 and the outer diameter of the shaft 301. The resulting image would therefore include portions that correspond to the interior of the shaft. Accordingly, image processing can be performed such that distance $c1$, $c2$, or $c1+c2$ is masked out in the displayed image. In the case where $c1$ and $c2$ are masked out, only the area $c3$ would show up on the image (where the total imaging distance or capability of the fiber is equal to $c1+c2+c3$). For example, up to 100 pixels can be masked out, such as between 20 and 60 pixels, for example approximately 40 pixels.

Additional image processing is possible. For example, the image can be corrected to account for lag of the optical fiber in the amount of rotation at the handle vs. at the distal end of the catheter. Images for lag correction can be captured automatically. Further, images can be exported and stored, for example in a movie format. The images can optionally viewed in adjustable grayscale. Further, the speed of the waterfall view can be adjusted. In some variations, and offset or "ghost" image may be overlaid atop the OCT to indicate the difference between the predicted and actual rotational orientation of the catheter.

The catheter variation described immediately above provides an internal motor for rotating the distal tip. In some variations, a manually rotatable device may be used with an adjunctive device providing a motorized movement of the distal tip. In this variation, the handle portion of the device may set and be secured within a housing that includes a motor and gearing to automatically rotate the distal tip at a predetermined or adjustable speed. Thus, this motorized accessory device may adapt an otherwise manual device to automatically rotate.

Other variations of catheters are possible that include one or more of the features described above.

Figure 11A:
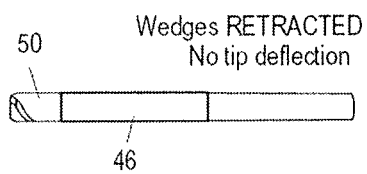
FIGS. 11A-11C illustrate one variation of an exemplary catheter having a rotating distal tip region (housing and wedges extendable from the housing) with the rotating wedges retracted into a rotating housing (FIG. 11A); with the rotating wedges extending from the rotating housing (FIG. 11B); and with the distal end region deflecting (FIG. 11C).
Figure 11B:
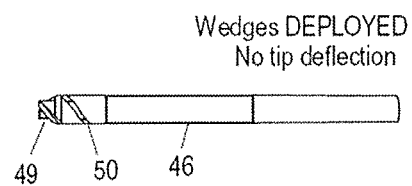
Figure 11C:
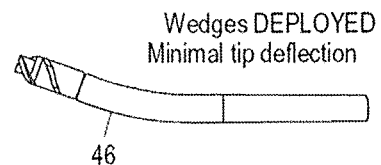

In some variations, the rotatable distal tip includes a fixed or rotatable housing from which dissection elements may extend or retract. An imaging element, such as an OCT imaging element, may be included in this embodiment as well. Referring to FIGS. 11A-11C, in some variations, wedges 49 may be extended from a rotatable distal tip 50. In FIG. 11A, the device is shown with the wedges retracted into the rotatable distal tip 50. In FIG. 11B, the wedges 49 have been extended from the housing 46. The distal end of the device can be shared and is shown deflecting upwards (steering in one plane) in FIG. 11C while the wedges are extended from the housing.

Both the distal tip and the wedges can be configured to rotate. The wedges 49 (which may be sharp blades or may be blunt) can be extended from the distal housing and locked in any position (extended, partially extended or retracted) and rotated clockwise and/or counterclockwise while locked in a retracted, extended or partially extended position.

The wedges may be fully or partially retracted into a distal housing. The extension of the wedge from the distal housing may be limited. For example, the wedges may be prevented from extending fully out of the distal housing, thereby preventing material (such as a plaque or tissue) from getting caught between the wedges and the housing.

The wedges at the distal end may be referred to as a blade or blades, even though they may be substantially blunt. In some variations the wedges are configured so that they are forward-cutting, but not side-cutting. This means that they may include a forward-facing cutting edge, and the more lateral edges may be blunted or less sharp. In some variations, the rotating distal tip includes only a single wedge, rather than multiple wedges. The wedge (blade) may be helically arranged at the distal tip.

In one embodiment, the rotating distal end comprises two or more wedges that are radially separated around the tip region (e.g., spaced equally apart radially). It may be advantageous to have three or more wedges spaced around the tip, which may improve centering of the device, as described herein.

In the examples provided above, the distal tip of the device is rotated through multiple complete rotations (both clockwise and counterclockwise) to move the distal tip and/or any attached imaging sensor in rotation around the elongate longitudinal axis of the device. In some variations the distal tip of the device (including the atherectomy devices described below) may be rotated through partial rotations. This is illustrated in FIGS. 12A-13D. In this example, a driveshaft rotates continuously in one direction, e.g., clockwise, but this one-directional rotation is translated at the distal end of the device into oscillating motion.

Figure 12A:
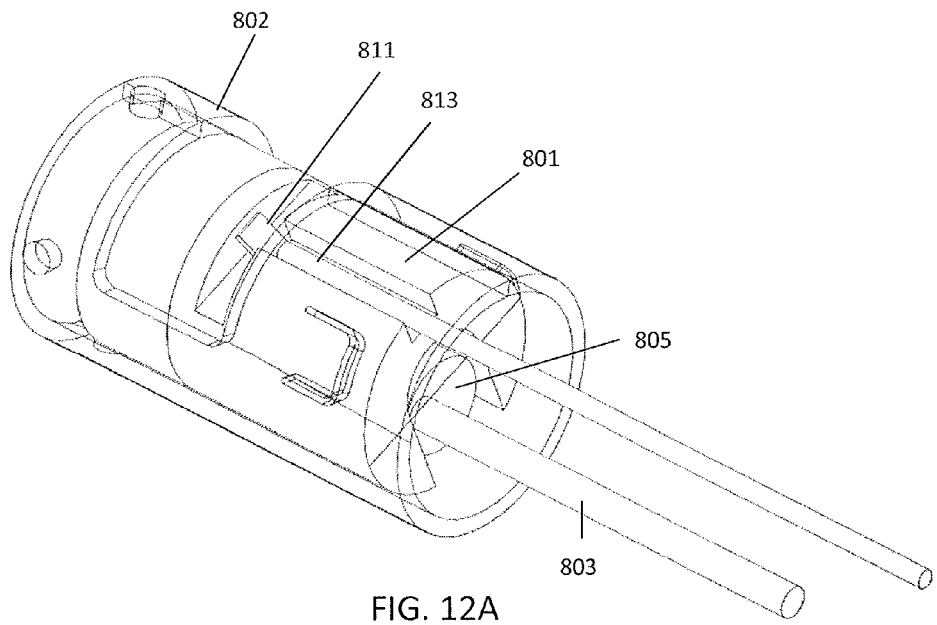
FIGS. 12A and 12B show isometric views of one variation of a system for oscillating the distal end of a catheter, which may be used as part of a catheter device.

FIG. 12A shows a partially transparent view of one variation of an oscillatory motion system for rotating the distal end portion of a catheter back and forth (clockwise and counterclockwise) though a partial rotation, such as less than 360 degrees, e.g., less than 180 degree, etc. In this example, the system is shown connected to an oscillation/rotating element 801 to which the imaging sensor, including a mirror 811 and the distal end of an optical fiber 813 for the exemplary OCT system, are connected. Thus, oscillation of the oscillation/rotating element 801 moves the OCT sensor to image an angular view of the field of view. The oscillation/rotating element 801 may be moveably housed within an outer housing 802 which may remain "fixed" relative to the inner oscillation/rotating element 801. The outer housing 802 may be connected to the rest of the catheter. In some variations, this catheter is strictly configured for OCT imaging and is not configured for atherectomy or for guidewire positioning.

Figure 12B:
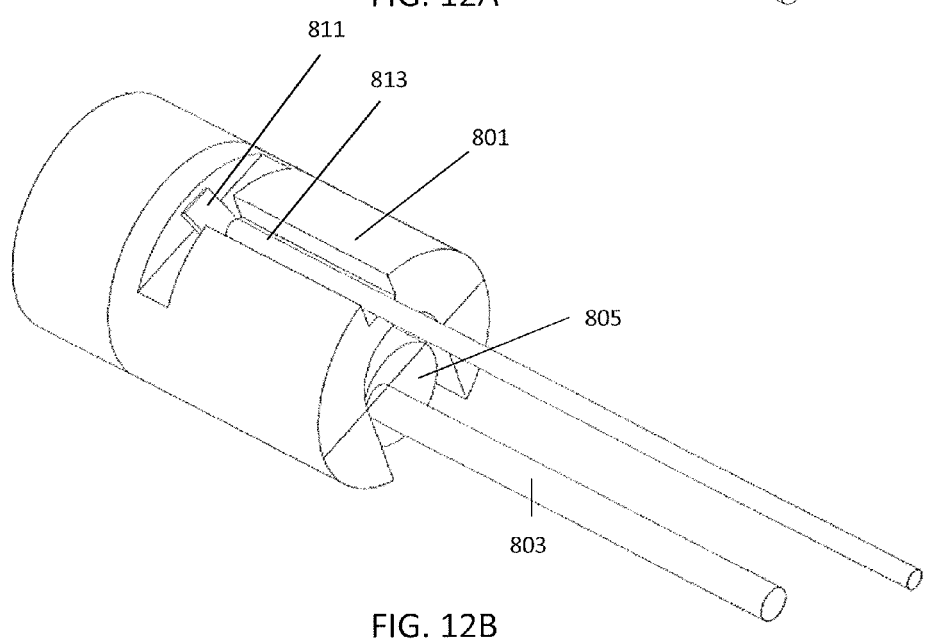

FIG. 12B shows the device of FIG. 12A with the outer housing 802 removed. The oscillation/rotating element 801 includes a C-shaped end region into which a camming member 805 that is attached to the rotating/rotatable driveshaft 803 is housed. The camming member 805 in this example is a cylindrical member to which the driveshaft 803 is eccentrically connected, so that the center of the longitudinal axis of the driveshaft 803 is off-axis for the center of the longitudinal axis of the camming member 805. This is illustrated in FIG. 13A, which shows the camming member 805 and attached driveshaft 803 within the C-shaped cut-out of the oscillation/rotating element 801.

In operation, rotation of the driveshaft will rotate the camming member 805 as illustrated in FIGS. 13B-13D, pushing the oscillation/rotating element 801 first clockwise, then counterclockwise to subtend an arc within the outer housing. This motion thereby allows scanning of the OCT imaging system across this arc. The larger the camming member and/or the greater offset of the driveshaft and the camming member, the greater the arc traversed by the oscillation/rotating element 801.

Figure 14A:
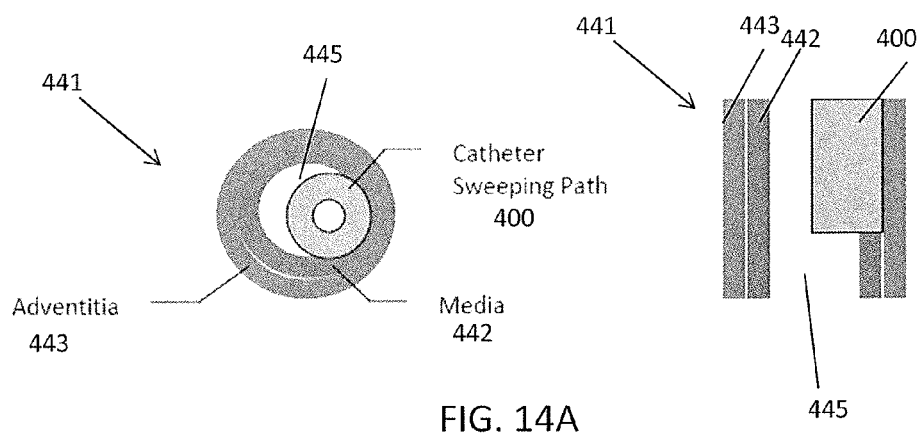
FIG. 14A shows cross-sections though a vessel with a catheter located in the true lumen (e.g., surrounded by both the adventitia and media)
Figure 14B:
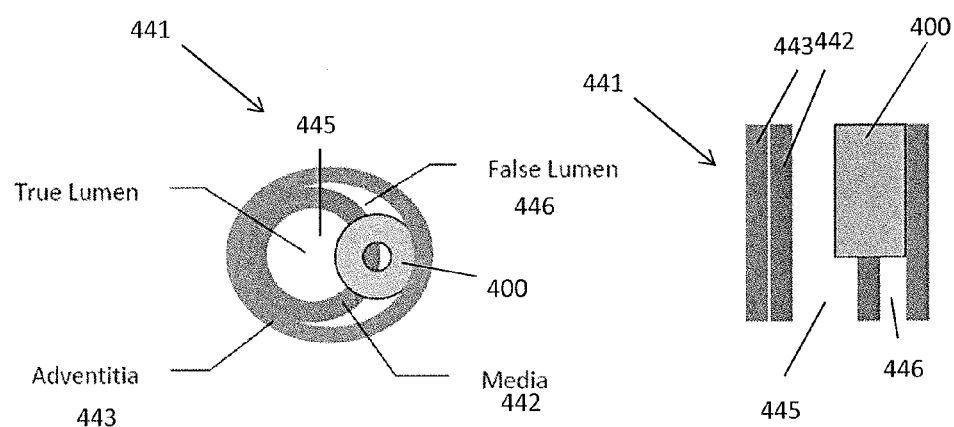
FIG. 14B shows cross-sections through a vessel with a catheter located in the false lumen (e.g., between the adventitia and the media).

As mentioned above, any of the catheters described herein may be used to treat peripheral vascular disease. In particular, the catheters may be used to place one or more guidewires across an occlusion, so that the occlusion may be imaged, removed, and/or displaced. Referring to FIGS. 14A and 14B, in some variations, the devices described herein are centering or self-centering within the lumen of the vessel. The vessel 441 (shown in cross-section on the left a transverse section on the right of each figure) includes the media 442 (e.g., tunica media) surrounded by adventitia 443 (e.g., tunica adventitia). During operation, it is desirable that the devices 400 remain centered within the "true" lumen 445 (the center) of the vessel 441 as shown in FIG. 14A, rather than a "false" lumen 446, i.e., the region between the adventitia 443 and media 442 as shown in FIG. 14B. If the catheter device does end up in the sub-intimal plane (e.g., false lumen 446), as illustrated in FIG. 14B, the device may reside between the media 442 on one side and the adventitia 443 on the other. To ensure that the devices described herein end up in the true lumen 445, the devices may be configured for both passive centering (self-centering) and active centering (including a centering mechanism).

In some configurations, the devices described herein are self-centering and are thus configured to help maintain the catheter (e.g., the tip of the catheter) within the true lumen. When used to treat chronic total occlusions, the manually or automatically rotatable distal end of the catheter may guide the catheter in the true lumen, especially when the reaching the distal cap of a lesion. For example, because the diameter of the rotating distal end may be at least equal to the diameter of the more proximal regions of the elongate body of the device, the tip may be sufficiently blunt to passive self-center within the lumen of a vessel. However, if the device does end up within the "false lumen," it can be configured to self-center back into the true lumen. That is, the elastic nature of adventitia typically prevents the tip from engaging and tearing the tissue. At the same time, it is easy for the rotating tip to engage with the media if it is presented in the front of the device, which may include the tissue-cutting surface(s). Thus, the rotating tip may selectively dissect its way through the media and not through adventitia. Once the device dissects its way through the medial, it returns to the true lumen.

Although centering (self-centering) of the catheter may result from the rotation of the distal end for the dimensions of the devices illustrated herein, one or more additional centering features may also be used to help the device to stay in true lumen of the blood vessel. Thus, in some variations, the catheter may be configured for use with one or more centering features to help prevent the distal tip from leaving the true lumen. The centering feature may project from the distal tip, the lateral sides of the distal tip, or the lateral sides of the distal end region, e.g., proximal to the distal tip.

In some variations, the centering feature is a balloon that expands (or is expandable, inflatable, or otherwise extendable from the lateral sides of the distal end region of the device) to keep the distal tip centered in the lumen. The device may also be deflectable or steerable at the distal tip region, as previously described, and/or may include one or more sensors (e.g., OCT imaging as described above), to help detect when the tip is approaching or has passed into the false lumen or otherwise left the true lumen.

For example, FIG. 15A illustrates one variation of a catheter (as described in patent application U.S. Ser. No. 12/689,748, previously incorporated by reference) which may have a rotating distal tip region. FIG. 15B shows a catheter 500, similar to the catheter of FIG. 15A, but including a balloon 522 located proximal to the rotating distal tip. Although only this catheter design is shown with the centering mechanism, it is to be understood that the centering mechanism could apply to any of the catheter configurations described herein. In some variations, the balloon may cover or extend over the rotating distal tip region. In this example, the distal end region (proximal to the distal tip 101 that rotates) may include a balloon 522 that is collapsed around the outer diameter of the catheter shaft 103, but may be inflated and expanded against the walls of the vessel. In addition to centering the distal end of the catheter shaft 103, expanding the balloon 522 may also expand the opening or passageway through the vessel. This may, in turn, improve treatment outcomes with the device, perhaps by loosening or preparing the atheroma (or other occlusion) for removal or displacement. In FIG. 15B, the proximal region of the catheter shaft 103 includes a port 524, for example a y-type connector, for inflation fluid, that may be use to inflate and deflate the balloon 522. Any appropriate inflation fluid may be used, including water, saline, lubricant, dye, or some combination of these.

Figure 16A:
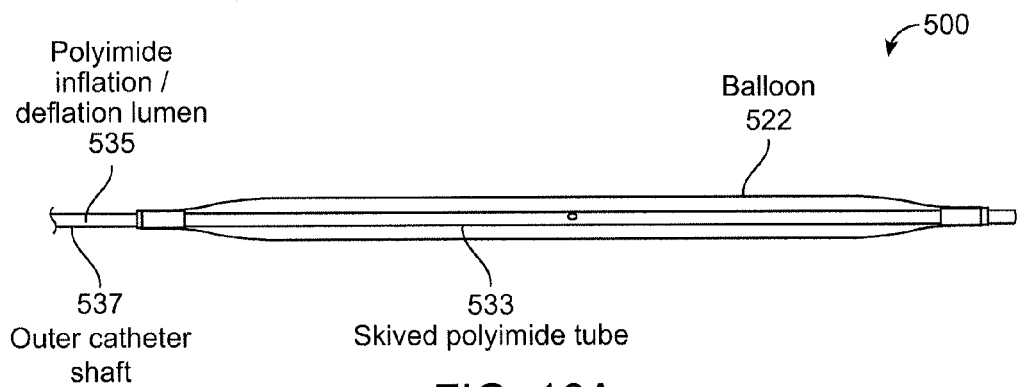
FIG. 16A shows the distal end of one variation of an exemplary catheter having an inflatable centering feature.
Figure 16B:
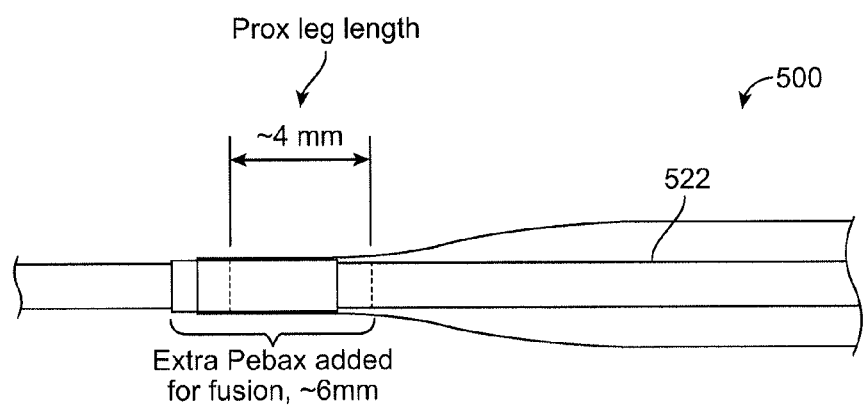
FIGS. 16B and 16C show enlarged views of the proximal and distal ends of the inflatable balloon region of the catheter of FIG. 16A, respectively.
Figure 16C:
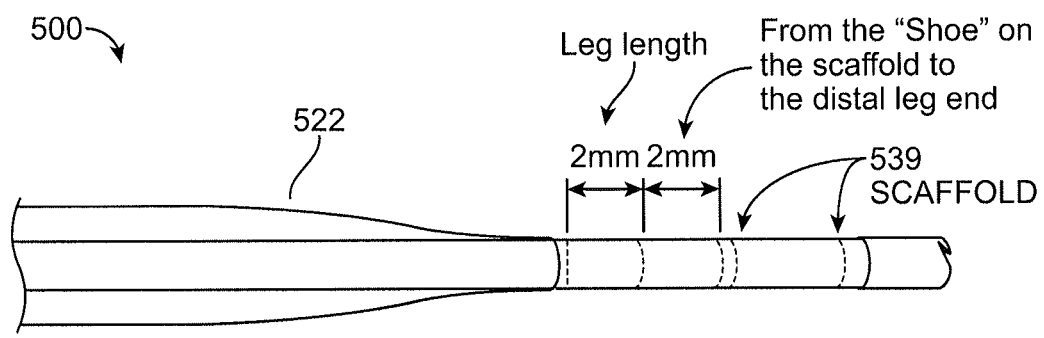

In this example, the catheter 500 is fabricated similarly to the catheters described previously, i.e., to include an inner lumen for passage of a guidewire, surrounded by a driveshaft for rotating/oscillating the distal tip, and again surrounded by an outer diameter jacket (e.g., of a flexible, braided stainless steel, polymer, etc.). Referring to FIGS. 16A-16C, prior to lamination of the outer jacket 537, on the outer catheter, an additional tube 533 to form the inflation lumen 535 (e.g., a 0.011" ID polyimide tube) is fused along the side of the outer catheter during lamination. A mandrel 539 (e.g., a 0.009" stainless steel mandrel) may be inserted during assembly processing to insure patency of the inflation lumen, and removed upon completion.

A balloon 522 (e.g., formed by nylon extrusion) may be attached near the distal end (e.g., proximal to the distal end of the catheter 500, as illustrated in FIG. 15B, and also FIGS. 16A-16C. The balloon 522 can have a nominal dimension of approximately 10 cm in length and a diameter of 5 mm (expanded). The balloon 522 has two rounded shoulder regions, one at the proximal end and one at the distal end; in some variations one or both ends may be tapered. In FIG. 16A-C, the inflation lumen ends between the proximal and distal end of the balloon, e.g., near the center of the balloon, and terminates in a skived opening to allow entry/exit of inflation material. In some variations, the balloon 522 has a slightly smaller diameter at the proximal end compared to the distal end to compensate for the missing inflation lumen at the distal end; thus, the overall outer diameter of the catheter 522 may be remain relatively constant.

The balloon 522 may be fused to the outer portion of the distal end of the catheter, as shown in FIGS. 16A-C. For example, a short length of PEBAX tubing may be added to the shaft at the locations where the distal and proximal ends (legs) of the balloon will be located. These PEBAX lengths may be used to ensure that enough material seals and fuses the balloon to the outer shaft. FIGS. 16B and C show the fused proximal ("rear leg") and distal ("front leg") regions of the balloon. Prior to fusing the balloon 522 to the shaft, the inflation lumen 535 (polyimide tube) is skived at the distal end to correspond to a location of the distal inflation/deflation hole approximately midway along the length of the balloon 522. The balloon 522 may be folded, sealed and/or heat set (e.g., to maintain the small delivery diameter, etc.). For example, the balloon 522 may be pleated, folded and heat set.

Figure 17:
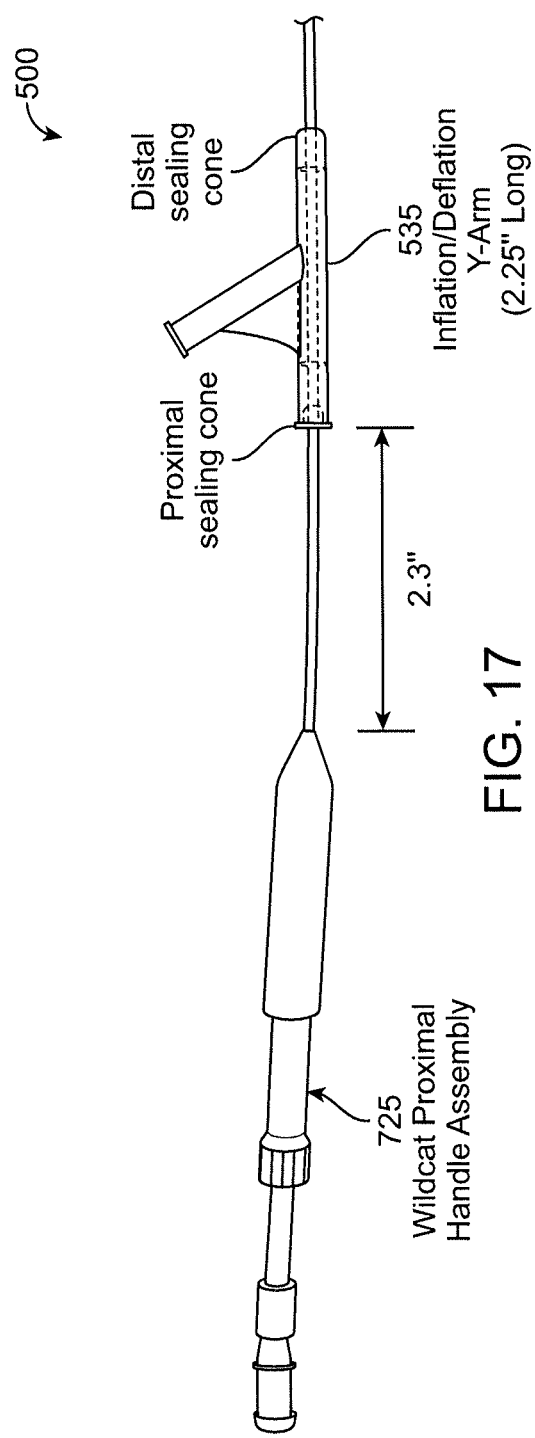
FIG. 17 shows one variation of a handle region of the catheter of FIG. 16.

FIG. 17 shows one variation of the handle region 725 of a catheter 500 including a balloon-type centering feature. In this example, the proximal end of the device includes a Y-arm with an inflation/deflation port or lumen 535, and sealed in position, to prevent leakage. In some variations, a separate inflation lumen is not included, but all or a portion of the region between the outer sleeve and the inner catheter (e.g., the central or offset guidewire lumen) is used as the inflation lumen connecting the inflation port to the balloon.

The dimensions of the entire catheter, including the balloon and distal end region may be adjusted. In one example, the dimensions (un-inflated) are approximately: proximal shaft has a diameter between about 0.074 inches and 0.084 inches; the mid-shaft region has a diameter between about 0.074 inches and 0.079 inches; the proximal balloon leg has a diameter between about 0.085 inches and 0.094 inches; the distal balloon leg has a diameter between about 0.079 inches and 0.085 inches; and the mid region of the balloon over the inflation lumen has a diameter between about 0.077 inches and 0.085 inches. The double wall thickness of the balloon is approximately 0.0045 inches, and the catheter has a length from the distal end of the proximal assembly to the distal tip of the device of 111 cm, while the length from the distal end of the Y-arm to the distal tip of the device is approximately 91 cm. When inflated to 6 atm pressure, the balloon has a proximal diameter of about 0.218 inches, a mid-diameter of approximately 0.211 inches, and a distal diameter of approximately 0.210 inches (at 10 atm in this example, the proximal diameter was about 0.222 inches, the mid-diameter was approximately 0.216 inches, and the distal diameter was approximately 0.215 inches.

Figure 18:
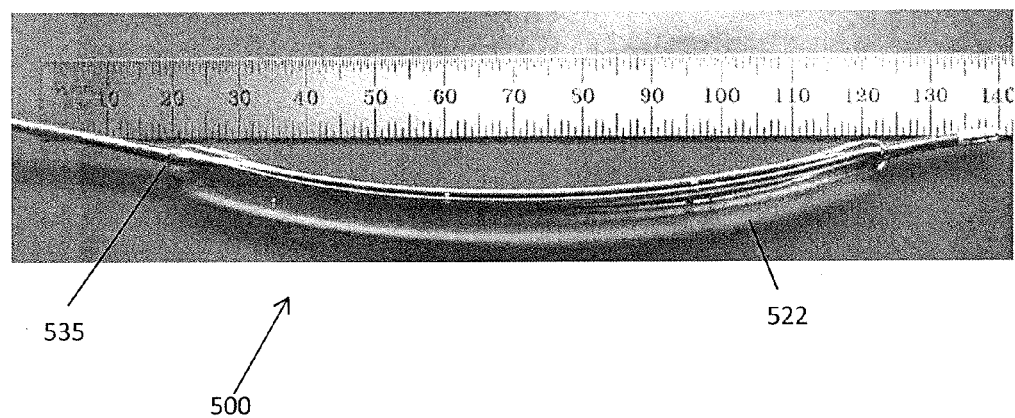
FIG. 18 shows the catheter of FIGS. 16A-17 with the inflatable centering feature inflated.

FIG. 18 shows one example of the catheter 500 with a balloon 522 inflated to approximately 6 atm with water. Deflation may be achieved using the inflation/deflation lumen 535. In one example, complete deflation took approximately 3 min. However, this may be faster or may be performed slower by adjusting the annular size of the inflation lumen or the viscosity of the inflation fluid. The balloon 522 was deflated until little or no residual inflation fluid was present in the balloon.

FIGS. 19A-C illustrate the balloon 522 of FIG. 18 after deflation and removal of the inflation fluid. In this example the balloon 522 has not been folded and/or pleated (or heat-set into this folded/pleated configuration), so the balloon collapses as shown. In some variations, the outer diameter of the catheter may be kept small in the deflated configuration.

Other variations of centering feature may be used as well, not limited to the annular/toroidal balloon described above. For example, in some variations one or more arms may extend from the outer shaft of the device and apply lateral force against the walls of the vessel to center it within the lumen. Alternatively, a coil located near the distal end and coiling around the distal end region may be expanded to extend loops outward and center the device. Any appropriate material, including shape memory materials (e.g., nickel titanium) may be used, and the centering feature may be configured to be atraumatic when contacting the vessel lumen (e.g., having rounded or flat, large-diameter tissue-contacting surfaces, etc.).

The guidewire positioning devices described herein may be configured as single-use, over-the-wire, devices. For example, the device may be compatible other guidewires of standard sizes used in minimally invasive procedures. The outer diameter of the elongate device (including the distal end region) may fit within a 7F sheath. The devices may be used with any appropriate guidewire, including steerable guidewires. For example, the guidewire may be a 0.035" guidewire. These devices may generally be described as "steering" a guidewire, although they may be used with a guidewire within the catheter, or the guidewire may be positioned within the device after the catheter has been positioned.

In general, these devices may provide support and guidance for positioning a guidewire across an occlusion. As described herein, the devices may support probing and exchange of an assortment of guidewires, by traversing an occlusion in a vessel. Typically, the catheters are inserted ahead of the guidewire (or with the guidewire retracted within the catheter) to provide a safe pathway thorough the occluded vessel, and thereby reduce or eliminate unnecessary damage to the vessel. In addition, the devices described herein may be used to deliver contrast. The internal lumen which may be used by the guidewire and/or the outer lumen may also be used for local dye or fluoroscopic contrast injections without removing the device from the vessel.

In operation, the rotating/oscillating distal tip allows the device to be passed through an occlusion such as a plaque occluding a blood vessel (or artery) without requiring removal of the plaque. Thus, the device may be used to bluntly form a pathway through a plaque using the retractable/extendable rotating wedges at the distal tip, or simply using the rotating distal tip alone. The cutting edges at the distal tip may also allow for helical and blunt microdissection. It is important to note that the catheter may be used without substantially dissecting or cutting the tissue, and that the distal tip is not necessarily intended (and may not) remove tissue, but merely form a passage through an occluded vessel. Once in position, the guidewire may be used to insert other devices, including atherectomy catheters.

In some variations, the cutting edges at the distal tip are sharp (e.g., cutting or knife-edged), while in other variations the cutting edges are substantially blunt. The cutting edges are typically curved around or along the longitudinal axis of the distal tip. For example, the cutting edge may extend helically around the distal tip end of the device.

In some variations, the catheters described herein may be used (e.g., inserted) in to the body in a 7F guide sheath for placement into the body. In general, the elongate catheter is flexible, and the outer surface(s) may be coated so that the catheter can be readily inserted into a lumen of a sheath, catheter, or directly into a body lumen. The elongate outer sheath is typically tubular, and may be coated (either or both inner and outer diameter surfaces) with a protective cover. The elongate outer sheath may be referred to as a shaft (e.g., catheter shaft), and may be coated with a lubricious material or may be formed of a smooth and/or lubricious material.

In some variations, the distal tip of the catheter is retractable into an expanded approximately toroidal-shaped distal balloon that is expanded proximal to the distal tip. This variation may allow re-centering or re-orientation of the catheter.

As noted above, the distal end of the catheters described herein may be steerable. The distal end region may be steerable in any appropriate manner. In particular, the distal end region may be steerable by defecting in one direction (e.g., 'down') or in more than one direction (e.g., down/up, right/left, etc.). The degree of deflection may also be controlled. In some variations, the tip may be deflected a maximum of 10 degrees, 15 degrees, 20 degrees, 25 degrees, 30 degrees, 45 degrees, 60 degrees, 90 degrees, or any angle there between. In some variations the distal end region of the device is pre-biased to be straight. Therefore the straight configuration of the distal tip may be restored once the deflection (controlled at the proximal end) is restored to the straight configuration. In addition to be deflectable, in some variations the distal end of the device is flexible. The end region may include the tip (e.g., the rotating tip) or it may include the region immediately proximal to the tip. In general the "tip region" may refer to the rotatable tip region at the distal end. The deflection may be performed by any appropriate method, including a pullwire coupled to a hinged distal region, a prebiased curve which can be released (e.g., by a pullwire, etc.), etc.

Deflection or steering of the distal end may help with re-entry of the device. For example, the deflectable/steerable distal end region (which may be referred to as the "steerable tip") may allow the catheter to re-enter the true lumen of the vessel if it becomes subintimal (e.g., if it extends into the fascia or region around the vessel).

In some variations, as described above, the distal region of the catheter is prebent, e.g., includes a jog. In other variations, the catheter includes a bendable distal end. Steering these catheters may be aided by visualization and may include rotating the length of the catheter body, which may be guided by imaging. Rotation or turning of the catheter body may be used to orient the distal tip region because of the bend in the catheter, in both fixed bend and bendable catheters.

In general, the proximal handle may act as an interface with the operator, and may include one or more controls. The handle region may also include connections to power (e.g., in automatic rotating/oscillating variations), imaging (e.g., connection to imaging source and processing), or the like.

The devices described herein may be any appropriate length, but relatively short length catheters may be particularly useful. For example, the device may be approximately 100 cm, allowing the device to reach any occlusion down to the popliteal and ease physician handling outside the body. In other variations, the device is between about 50 and 150 cm, between about 70 and 120 cm, etc.

As mentioned, the distal tip may be driven by an elongate driveshaft (or "torque shaft") that extends the length of the device. This driveshaft is typically robust, allowing increased torque precision and manipulation during the operation. For example, the torque shaft may be made of a braided stainless steel material having a hollow lumen (forming or surrounding a central, e.g., guidewire, lumen of the device). Rotation of the driveshaft typically drives the distal tip rotation. The driveshaft is typically flexible and connects to the rotational control at the proximal end (e.g., handle). The distal tip, including the wedges and housing, may rotate both clockwise and counterclockwise.

The handle region at the proximal end of the device may also be adapted for handheld use. In particular, the controls at the handle region may be adapted so that the device may be manipulated by a single hand. In some variations the handle region may also include one or more indicators or displays for displaying the status of the distal end of the device. For example, the handle may include an indicator indicating the extent to which the wedges are extended from the distal tip. The indicator may be a dial, slider, or the like. The indicator may be marked or unmarked. The proximal handle may be otherwise configured to be handheld. For example, the controls may be clustered or located at one end of the handle with a gripper region at the other end. For example, the controls may be clustered at the proximal portion of the handle (allowing the distal portion of the handle to be gripped in the palm of the hand, and manipulated by the thumb and forefinger of the right.

In general, the elongate outer sheath of the catheter is flexible, and may be coated so that it can be readily inserted into a lumen of a sheath, catheter, or directly into a body lumen. For example, the elongate outer sheath of the catheter may be formed of a braided stainless steel, a polymer, or the like. The elongate outer sheath is typically tubular, and may be coated (either or both inner and outer diameter) with a protective cover. The elongate outer sheath may be referred to as a shaft (e.g., catheter shaft), and may be coated with a lubricious material or may be formed of a smooth and/or lubricious material.

The dimensions of the devices described herein (including in the figures) may be varied while staying within the scope of the invention as generally described. Unless otherwise indicated, these dimensions are intended as merely illustrative and not limiting.

As mentioned briefly above, various aspects of the devices described herein provide substantially benefits compared to other device which may be used in occluded vessels, including rotating devices. For example, the forward cutting blades may prevent cutting on the sides/walls of the lumen. This configuration may also help with self-centering, as mentioned. In addition, the device may be configured so that the diameter of the blade (e.g., wedge) region is the same as the diameter of the rest of the catheter. Thus, the diameter of the distal end having the rotatable wedge is maximized so that the blades are the same crossing profile as the rest of the catheter, which may allow for optimal engagement within the occlusion in the vessel.

In some variations, the guidewire lumen described herein is not central, but is offset along all or a portion of the length of the device. The lumen (or a separate lumen) may also be used to pass a material such as a contrast dye, saline, an imaging device, etc. An outer lumen may surround the inner (guidewire) lumen, and may enclose this space to form a separate lumen in which one or more additional lumens (e.g., inflation lumen in variations including a balloon or expandable feature) may be included; a driveshaft for rotating or controlling rotation of the distal tip may also be included.

As described above, the proximal end of the device typically includes a handle region that may be used to control the distal end. For example, the device may include a rotation control, a wedge articulation control and/or a steering control. In some variations these controls may be combined into one or more controls or these functions may be distributed or divided between different controls. Any appropriate control may be used, including slides, knobs, dials, buttons, levers, switches, etc. In some variations the controls may be automated or computer-controlled. In some variations a driver (e.g., motor, mechanical driver, etc.) may be used to drive the controls. For example, rotation of the distal tip region may be driven by a motor, and may be geared or otherwise controlled. The rotation may be manually or automatically controlled.

Part II: Atherectomy Catheters

One variation of an atherectomy catheter (which may be used after placement of a guidewire as described above) is illustrated in FIGS. 20A-22D and described below. In general, an atherectomy catheter may access the vasculature using conventional catheterization techniques employing sheath and/or guiding catheter access and tracking over a positioned guidewire. The device may track through the vasculature to the target lesion. A fiber (e.g., a Single Mode fiber) can be positioned at or near the distal assembly of the device and to enable imaging (e.g., OCT imaging) to be used for lesion assessment and treatment planning. For example, the device may be rotationally oriented toward the diseased sector of the artery, and activated using proximal physician controls to preferentially expose the cutting edge to the diseased tissue. In the variation described herein, a circular cutter will begin rotational movement at approximately 10 to 10000 revolutions per minute (rpm) of the driveshaft. The device may be translated through the lesion to plane and cut the diseased tissue while the OCT image provides real time feedback regarding wall and disease characterization, cutter apposition and relative cut depth. During the cutting pass, the tissue may travel through the circular hollow cutter into a tissue reservoir that is distal to the cutter. Upon completing the cutting pass, proximal controls may be used to articulate the device, returning the cutter to its shielded position for further delivery and placement. Multiple runs through this procedure may occur to fully treat the disease.

Figure 20A:
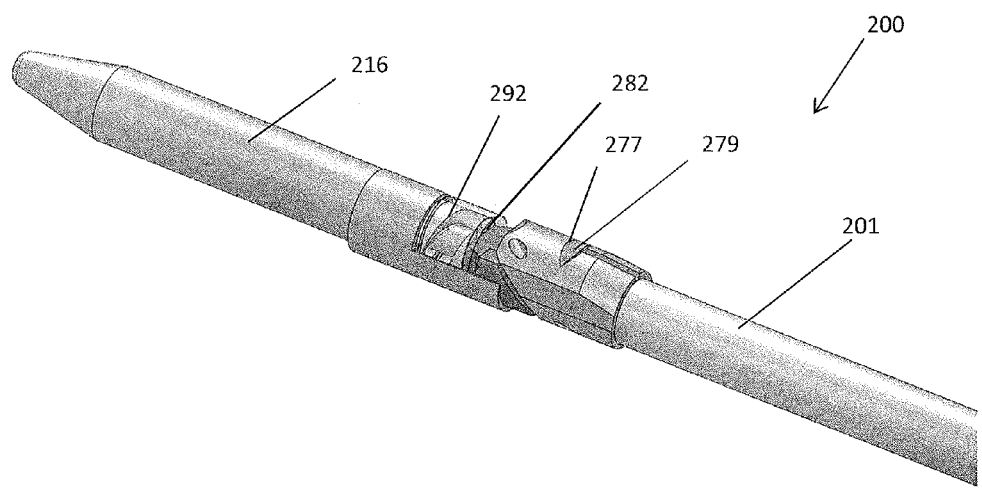
FIG. 20A shows an isometric view of closed/non-activated distal atherectomy device assembly.
Figure 20B:
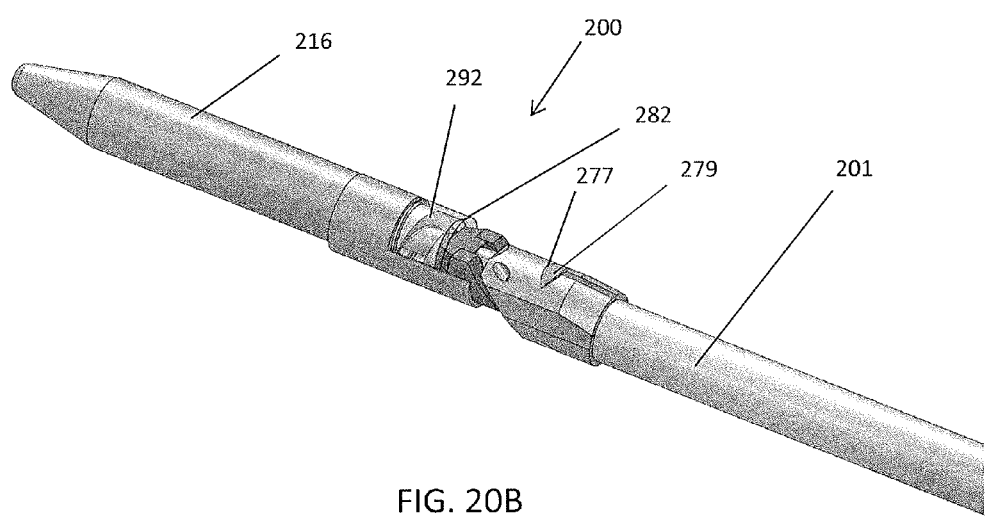
FIG. 20B shows the device of FIG. 20A in the active/open configuration.

FIGS. 20A and 20B illustrate one variation of an atherectomy device 200 as described. The device includes a cutter 282 rotatable by a driveshaft 294 (see FIG. 21) located within an elongated catheter body 201. The cutter edge, with a comparatively large cross-sectional area, is located along the circumferential surface of the main catheter body 201. The driveshaft 294, with a comparatively small cross-sectional area, is located within the central region of the catheter body. In some variations, the cutter diameter is at or near the maximum crossing profile of the main catheter body 201 to maximize cut tissue cross-sectional area and minimize depth of cut. The large cross-sectional area may provide more efficient cutting passes, thereby reducing the time of procedure, and may add a degree of safety by reducing the depth of cut required to achieve comparative luminal gain.

In some variations, at least some portions of the device 200 can be hollow. Accordingly, the cutter 282 can cut tissue from the wall of the artery, pass directly through the hollow portions, and be stored in a tissue storage area, such as tissue storage area 216.

Figure 21:
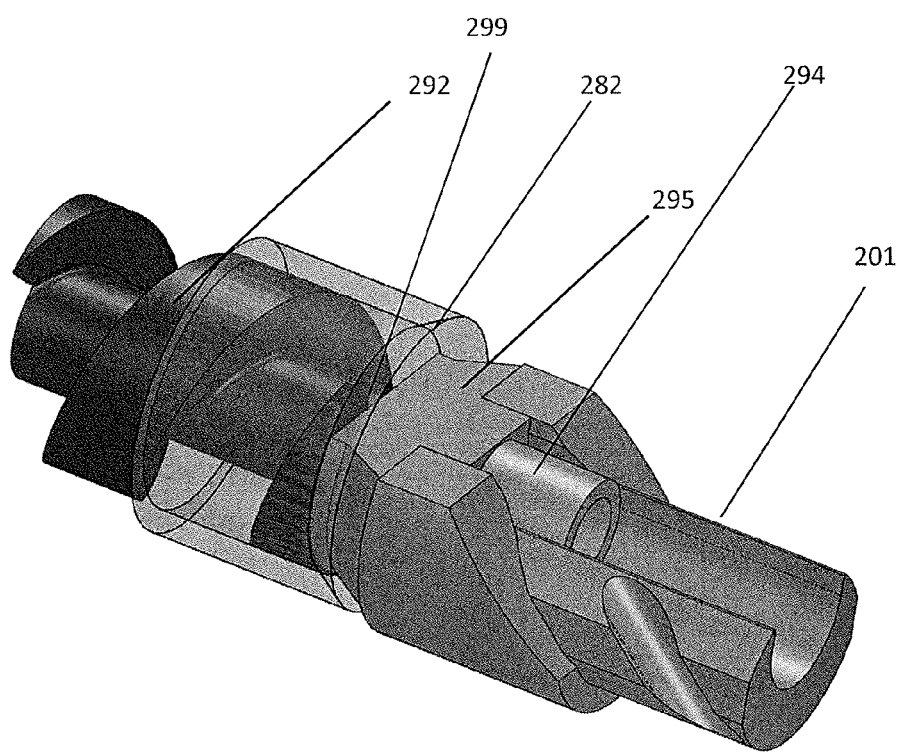
FIG. 21 illustrates the helical auger geometry of the atherectomy device shown in FIGS. 20A and 20B.
Figure 22A:
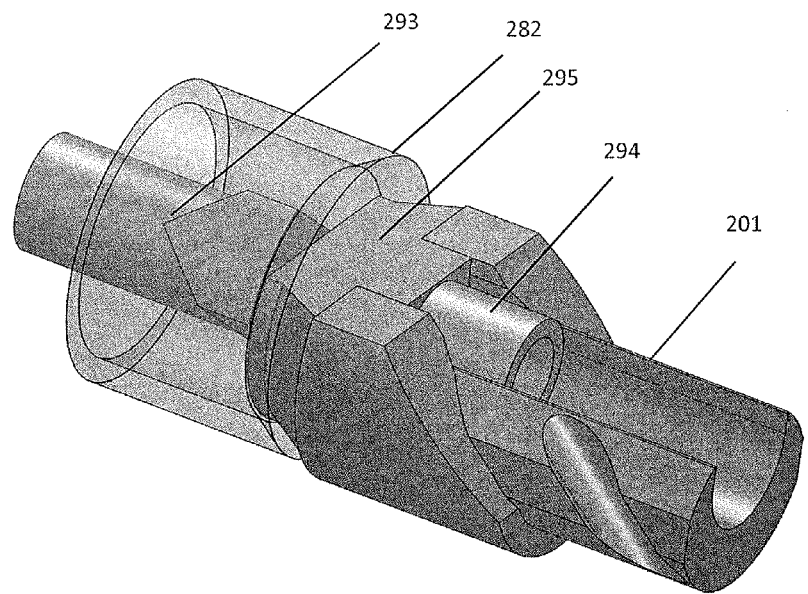
FIGS. 22A-22D show a variation of a distal atherectomy system with an auger component.
Figure 22B:
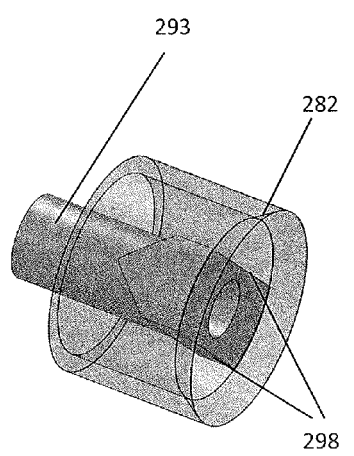
Figure 22C:
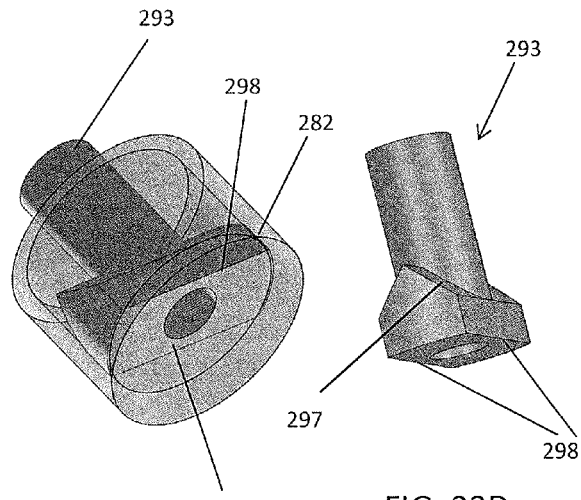
Figure 22D:
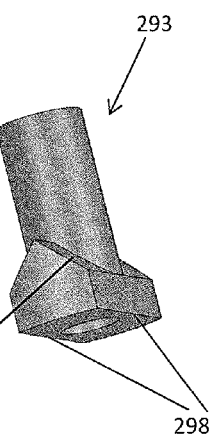

FIGS. 20A and 20B portray the distal portion of the device in both the non-activated (FIG. 15A) and activated (FIG. 15B) positions, respectively. In the closed/non-activated position, the cutter 282 is shielded to prevent unintended damage to the inner diameter of ancillary medical devices and vasculature. In the open/activated position, the cutter 282 is exposed with the tissue packing auger 292 distal of the cutting edge as shown in FIG. 21. In one pull-to-cut configuration for a rotational cutter edge catheter embodiment, the distal tip of the catheter is advanced past the targeted lesion. The catheter is delivered in the non-activated position where the delivery catheter and vasculature is shielded from the cutter edge. Once the cutter edge is positioned past the lesion and oriented for optimal tissue removal, the distal tip assembly is activated to present the cutter edge 282. The driveshaft of the catheter is powered to rotate the cutter 282 as it is passed across the lesion. The rotational motion assists the cutter in cutting the targeted tissue. After completing the cutting pass, the device is then returned to the non-activated position which assists the cutter in parting off the strip of tissue and packing it into the tissue storage lumen 216. The device 200 can include an imaging sensor 279 in a notch 277 near the distal end of the device. The imaging sensor 279 can be an OCT sensor similar to that described above.

Referring to FIG. 21, the driveshaft 294 can be directly connected to the circumferential cutter 282 and to an auger 292 or Archimedean screw. The driveshaft 294 can thus transmit torque to the cutter 282 while allowing tissue to pass through the hollow cutter 282 as it is rotated. In this configuration, as the cutter 282 is advanced across a tissue lesion in a pull-to-cut configuration, and the cutter 282 cuts the tissue from the vessel wall. With continued advancement of the cutter/auger assembly, tissue is then passed through the inner, hollow diameter of the cutter 282. As the tissue advances to the rotating auger component 292, the tissue is then cut into segments by the cutting edge 299 of the auger component 292 and passed into the tissue storage area 216 distal to the auger 292.

The system depicted in FIG. 21 shows the auger component 292 configured in a helical geometry. However, the auger component can have other configurations. For example, FIGS. 22A-22D show an auger component 293 that is capable of shearing tissue segments when rotated in either the clockwise or counterclockwise direction. The auger can be substantially T-shaped with two cutting edges 298. Rotation of the auger component 293 in either the clockwise or counterclockwise direction would thus cause shearing of tissue. Advantageously, by having two cutting edges 298, the auger component 293 can shear tissue two times per rotation of the driveshaft 294. The auger component 293 can further include angled surfaces 297 configured to push cut tissue distally into the tissue storage area 216. Because the auger component 293 can cut in both the clockwise and counterclockwise directions, it can work even if the driveshaft oscillates between clockwise and counterclockwise directions, as described above with respect to the driveshaft 421. In this configuration, the cutter edge can be configured for optimal cutting efficiency and is not limited to traditional, continuously rotating cutters.

Specifications of the driveshaft may balance flexibility to navigate tortuous anatomy and torsional/tensile/compressive rigidity to drive distal mechanisms through hard calcified tissues or tight lesions. In either the continuously rotating configuration or the oscillatory cutting configuration, the cutter concept can be configured in a push-to-cut configuration where the catheter is advanced to perform the cutting operation. Conversely, the cutter concept can also be configured in a pull-to-cut configuration where the catheter is retracted to perform the cutting operation. For the illustration purposes only, the description herein focuses on the pull-to-cut embodiment, though it should be clear that push-to-cut variations may be used as well. Common to all described embodiments, minimal longitudinal motion and translational deflection of the tip mechanism such that the tissue entry window is mainly defined by the vertical distance from the shear component base 295 to the cutter edge. This may prevent increased tissue invagination into the exposed tissue entry point with increased apposition force. Depth of cut will then remain relatively constant at varied force of engagement between cutter and tissue.

In a pull-to-cut configuration, the cutting edge orientation may be such that cutting of tissue is performed with longitudinal movement of catheter distal to proximal.

In some variations, the auger mechanism may be configured to function in a continuously rotating system where the auger is configured with a helical geometry 292. When oscillating the direction of rotation of the device driveshaft, the auger 293 may assume a geometry that is capable of shearing tissue segments in either direction of rotation.

As described above, any of these catheters may include imaging, including the atherectomy catheters. The imaging element can provide a cross-sectional view of vessel wall morphology in the cutting plane. Ultrasound and/or optical imaging technologies may be used. Optical Coherence Tomography (OCT) is one preferred method of image guidance. The OCT technology currently embodied on prototype devices is capable of achieving approximate 10 micron lateral resolution and requires fiber optic assembly diameters below 0.010 inches.

The device may thus include on-board and real time image guidance capabilities. This capability may require an imaging element, or energy emitting assembly, to be positioned at the distal portion of the device such that local images of the vessel may guide device usage. The distal energy emitter(s) may be positioned in multiple locations in fixed positions or embodied in a mating assembly that may translate in an eccentric lumen or in the hollow lumen of the driveshaft. The emitter may send and receive relevant light or sound signals at 90 degrees from the catheter axis or at angles up to approximately 50 degrees to visualize distal or proximal wall features from a fixed position.

The emitting element may be positioned distal and/or proximal to the cutting edge. In a pull-to-cut configuration, proximal placement would provide information during a cutting pass prior to the cutter interacting with the tissue and, therefore, allow the physician to stop or continue cutting as disease changes in depth and/or position. Distal placement would also provide guidance regarding cut quality, depth and cutting efficiency.

Furthermore, the data collected at the distal end of the catheter, after transmitted and appropriately processed, may drive an automated means of cutter actuation. Increased amounts of disease detected by the software may automatically increase open distance between the cutter edge and the tip mechanism therefore increasing cut depth. Oscillatory cutter speeds may be adjusted according to feedback from the imaging system.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. A catheter device for crossing occlusions, the device comprising:
    an elongate body;
    a central lumen extending within the elongate body from a proximal end of the elongate body to a distal end of the elongate body;
    a rotatable tip at the distal end of the elongate body and configured to rotate relative to the elongate body;
    an OCT imaging sensor comprising an optical fiber, the OCT imaging sensor coupled with the rotatable tip and configured to rotate therewith, wherein the elongate body comprises one or more markers configured to occlude the OCT imaging sensor as the OCT imaging sensor rotates; and
    a bent or bendable region in the elongate body, the bent or bendable region forming or configured to form a fixed jog to point the distal end of the elongate body in a set direction, and wherein the one or more markers on the elongate body are in a predetermined circumferential position relative to the set direction so as to indicate an orientation of the distal end of the elongate body during OCT imaging.

2. The device of claim 1, wherein the fixed jog forms an angle of between about 10 to 45 degrees between the distal end of the elongate body and an area of the elongate body proximal to the fixed jog.

3. The device of claim 1, further comprising a drive mechanism configured to rotate the rotatable tip at between about 1 and about 100 rpm.

4. The device of claim 3, wherein the drive mechanism is configured to alternately rotate the rotatable tip in a first direction and a second direction.

5. The device of claim 1, wherein the rotatable tip comprises a helical blade edge.

6. The device of claim 1, wherein the rotatable tip comprises a substantially smooth, curved outer surface that presents an atraumatic tissue-contacting surface when rotated in the first direction and that presents a dissecting surface when rotated in the second direction.

7. The device of claim 1, further comprising a fluoroscopy marker on the elongate body, the fluoroscopy marker visible by fluoroscopy and configured so as to not obstruct imaging from the OCT imaging sensor.

8. The device of claim 7, further comprising a controller, the controller configured to align an OCT image generated from the OCT sensor with the fluoroscopy image using the fluoroscopy marker.

9. The device of claim 1, wherein a distal end of the rotatable tip is less than 3 mm from the imaging sensor.

10. The device of claim 1, wherein the central lumen extends through a driveshaft, the driveshaft configured to rotate the rotatable tip.

* * * * *